United States Patent [19]
Montzka et al.
[11] 4,016,167
[45] Apr. 5, 1977

[54] N-SUBSTITUTED-6,8-DIOXAMORPHINANS

[75] Inventors: Thomas Alfred Montzka, Manlius; John Daniel Matiskella, Liverpool, both of N.Y.

[73] Assignee: Bristol-Myers Company, New York, N.Y.

[22] Filed: Oct. 28, 1975

[21] Appl. No.: 626,393

[52] U.S. Cl. .................... 260/293.54; 260/293.55; 260/DIG. 13; 424/267

[51] Int. Cl.[2] .................................... C07D 221/26

[58] Field of Search ................ 260/293.55, 293.54, 260/DIG. 13

[56] References Cited

UNITED STATES PATENTS

| | | | |
|---|---|---|---|
| 3,853,889 | 12/1974 | Monkovic et al. | 260/293.55 |
| 3,891,657 | 6/1975 | Monkovic et al. | 260/293.54 |
| 3,910,920 | 10/1975 | Menard et al. | 260/285 |

OTHER PUBLICATIONS

May et al., J. Org. Chem. 26, 188-193 (1961).
Kugita et al., J. Org. Chem. 26, 1954-1957 (1961).
Murphy et al., J. Org. Chem. 25, 1386-1388 (1960).
Chignell et al., J. Med. Chem. 8, 235-238 (1965).
Saito et al., J. Org. Chem. 26, 4536-4540 (1961).
Eddy et al., "Synthetic Analgesics, Part IIB," Pergamon Press, New York, pp. 115-182.

*Primary Examiner*—G. Thomas Todd
*Attorney, Agent, or Firm*—Richard R. Lloyd

[57] ABSTRACT

N-substituted-6,8-dioxamorphinans have been found to possess potent narcotic agonist and/or antagonist activity. For example, the compound 17-cyclopropylmethyl-7,7-dimethyl-3-hydroxy-6,8-dioxamorphinan has been found to possess potent agonist-antagonist activity. These compounds are prepared by total synthesis and are not derived from opium alkaloids.

28 Claims, No Drawings

N-SUBSTITUTED-6,8-DIOXAMORPHINANS

BACKGROUND OF THE INVENTION

1. Field of the Invention

This invention embodies new and novel compounds useful as analgesics and/or narcotic antagonists and a new and novel total synthesis for their preparation.

2. Description of the Prior Art

A. Everette May and Hiroshi Kugita, J. Org. Chem. 26, 188 (1961) describe compounds having the formula

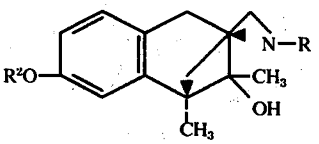

in which $R^2$ is H or methyl and R is methyl or phenethyl as being moderate to weak analgetics.

B. Everette May, Hiroshi Kugita and J. Harrison Ager, J. Org. Chem. 26, 1621 (1961) report compounds having the formula

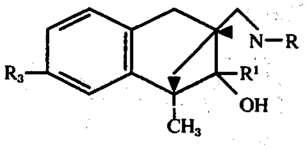

in which R is methyl or phenethyl, $R^1$ is methyl or H, $R_3$ is H, OH or methoxy as producing varying degrees of analgesia.

C. Everette May, Colin Chignell and J. Harrison Agar, J. Med. Chem. 8, 235 (1965) report compounds having the formula

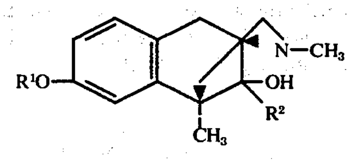

in which $R^1$ is H or methyl and $R^2$ is methyl as possessing analgetic activity.

D. Everette May and Hiroshi Kugita, J. Org. Chem. 26, 1954 (1961) report the compound having the formula

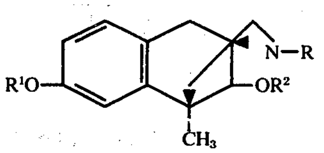

in which R is methyl or phenethyl, $R^1$ is H or methyl and $R^2$ is H or acetyl as having analgetic activity.

E. Everette May and Seiichi Sato, J. Org. Chem. 26, 4536 (1961) report compounds having the formula

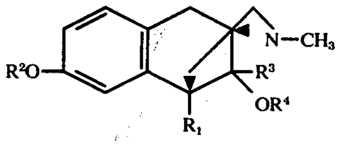

in which $R^2$ is H or methyl, $R^1$ is methyl or ethyl, $R^3$ is methyl or ethyl and $R^4$ is H or acetyl as possessing analgetic activity.

F. N. B. Eddy and E. L. May published a review of 6,7-benzomorphans in Synthetic Analgetics, Pergamon Press (1966).

G. U.S. Pat. No. 3,853,889 describes the compound having the formula

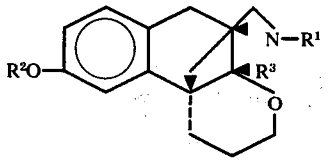

wherein $R^1$ is selected from the group comprising H, (lower)alkyl,

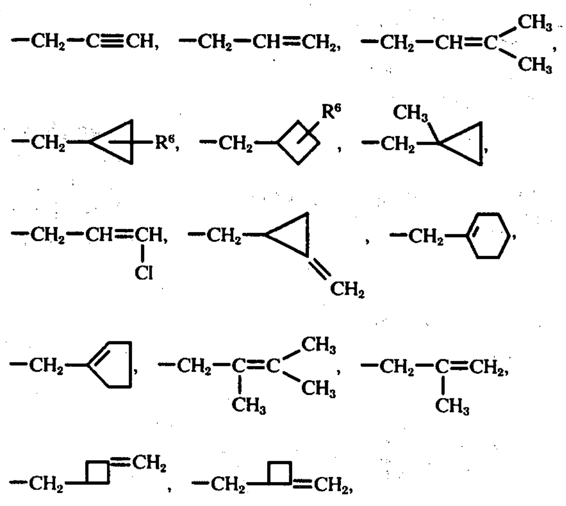

-continued

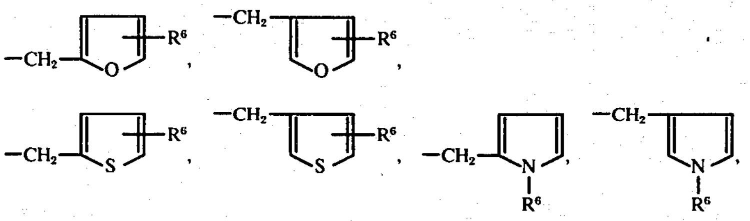

and (lower)alkenyl in which $R^6$ is H or $CH_3$, $R^2$ is selected from the group comprising H, (lower)alkyl,

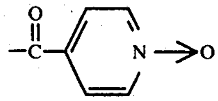 , (lower)alkanoyl , 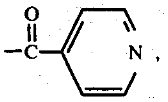

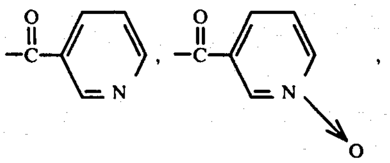

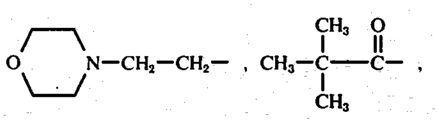

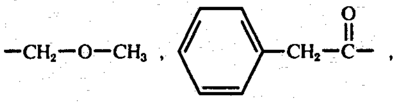

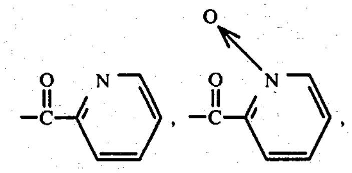

and cinnamoyl, and $R^3$ is H or (lower)alkyl; or a pharmaceutically acceptable acid acceptable acid addition salt thereof as possessing agonist/antagonist activity.

H. U.S. Pat. No. 3,891,657 describes the compounds having the formula

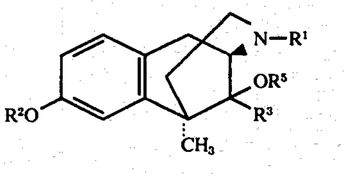

L wherein $R^1$ is selected from the group comprising $-CH_2-C$ $CH$, $-CH_2-CH{=}CH_2$,

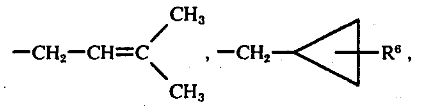

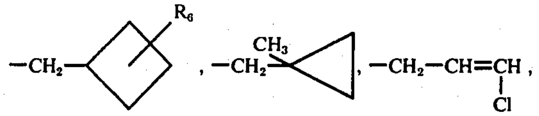

-continued

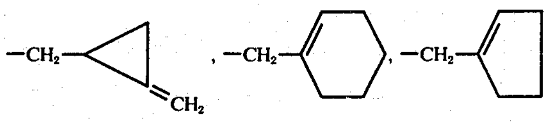

and (lower)-alkenyl in which $R^6$ is H or $CH_3$, $R^2$ is selected from the group comprising H, (lower)alkyl,

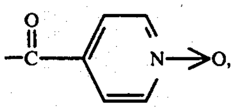 (lower)acyl, 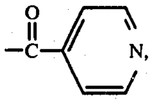

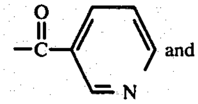 and 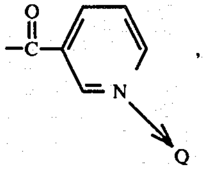

$R^5$ is H, (lower)acyl, trichloroacetyl or cinnamoyl; $R^3$ is H, $CH_3$, $C_2H_5$, n-$C_3H_7$, $-CH_2-CH{=}CH_2$ or $-CH_2-C$ $CH$, or a pharmaceutically acceptable acid addition salt thereof are analgetic agents, narcotic antagonists or intermediates in the preparation of such agents.

I. U.S. Pat. No. 3,285,922 reports morphinans and isomorphinans having the formula

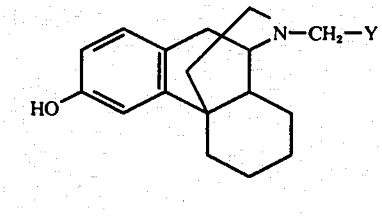

in which Y is cyclobutyl or cyclopropyl as possessing analgetic and/or narcotic antagonist activity.

J. M. Gates and T. Montzka [J. Med. Chem., 7, 127 (1964)] report the synthesis of morphinans and isomorphinans of the formula

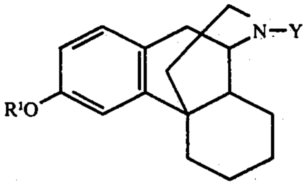

in which Y is cyclopropylmethyl, cyclobutylmethyl, -phenylcyclopropylmethyl, methyl, cyano, H, etc. and $R^1$ is methyl or H.

SUMMARY OF THE INVENTION

Compounds having the formula

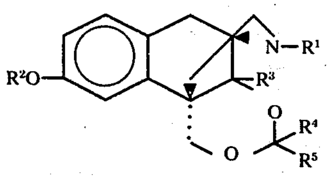

wherein $R^1$ is selected from the group comprising H, (lower)alkyl,

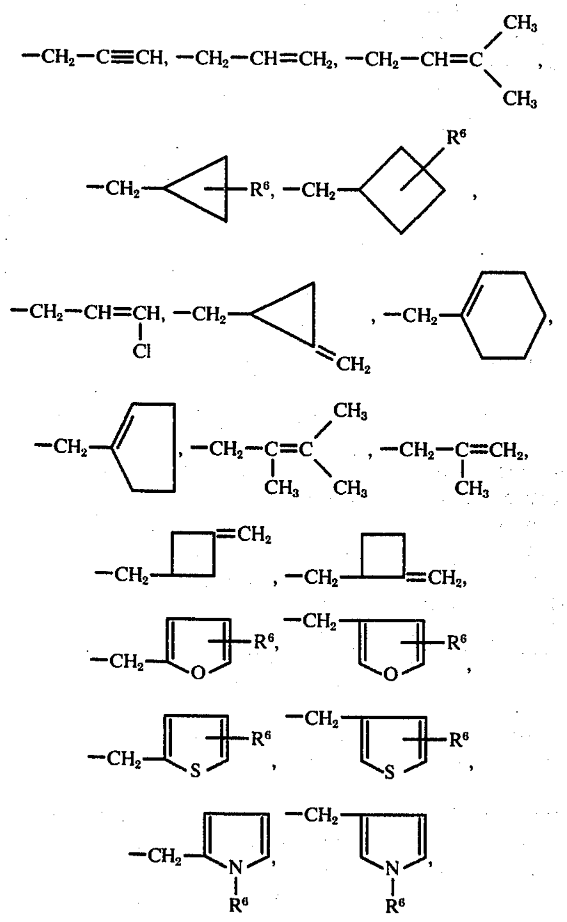

and (lower)alkenyl in which $R^6$ is H or $CH_3$, $R^2$ is selected from the group comprising H, (lower)alkyl,

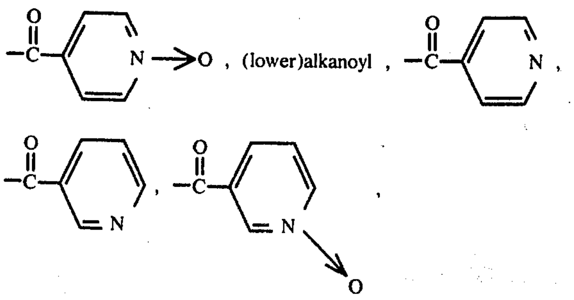

-continued

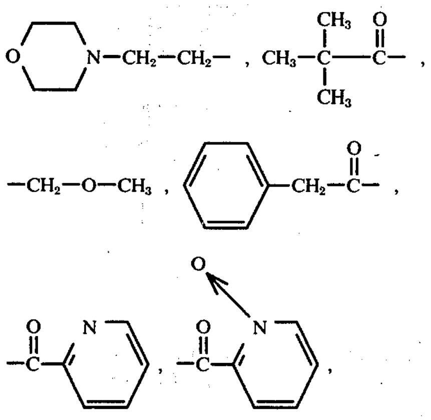

and cinnomoyl, and $R^3$ is H or (lower)alkyl; and $R^4$ and $R^5$ are alike or different and each is H, (lower)alkyl or trifluoromethyl, or when $R^4$ and $R^5$ are taken together they can represent a carbonyl function or a spirocycloalkyl group of 3 to 7 carbon atoms; or a pharmaceutically acceptable acid addition salt thereof possess potent agonist/antagonist activity or are useful intermediates.

DISCLOSURE OF THE INVENTION

This invention relates to the total synthesis of new and novel N-substituted-6,8-dioxamorphinans having the formula

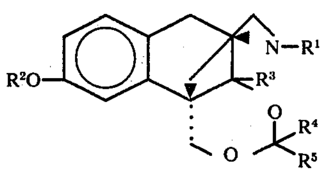

wherein $R^1$ is selected from the group comprising H, (lower)alkyl,

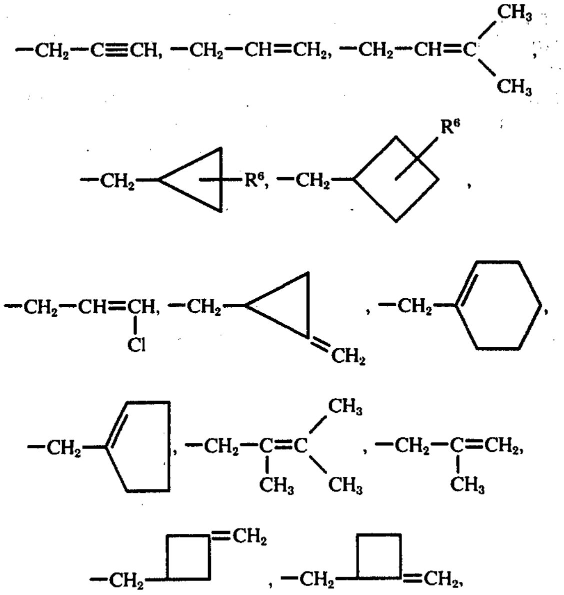

-continued

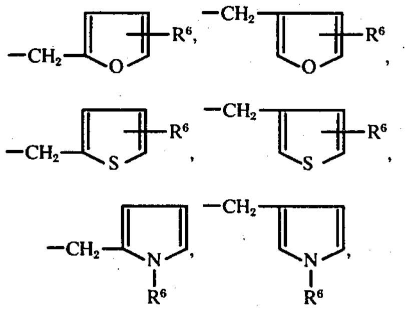

and (lower)alkenyl in which $R^6$ is H or $CH_3$, $R^2$ is selected from the group comprising H, (lower)alkyl,

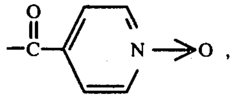 , (lower)alkanoyl , 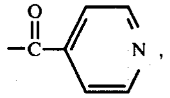 ,

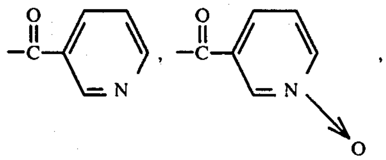 ,

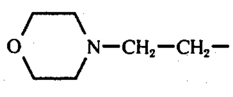 , 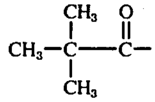 , $-CH_2-O-CH_3$ , 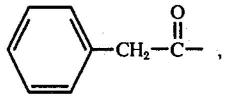 ,

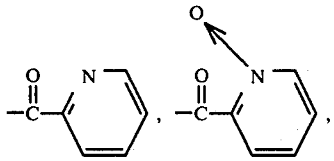 , and cinnamoyl, $R^3$ is H or (lower)alkyl and $R^4$ and $R^5$ are alike or different and each is H, (lower)alkyl or trifluoromethyl, or when taken together $R^4$ and $R^5$ are a carbonyl function or a spirocycloalkyl group of 3 to 7 carbon atoms; or a pharmaceutically acceptable acid addition salt thereof.

Drug abuse by thrill-seeking youth or by people looking for an escape from the realities of every day life has become more and more common place in our present society. One class of widely abused drugs are the narcotic analgetics such as codeine, morphine, meperidine, etc. It is because of the high addictive potential of these segments that much time and money are being expended by the pharmaceutical industry and by governments to try and discover and develop new non-addicting analgetics and/or narcotic antagonists.

It was therefore an object of the present invention to develop low abuse analgetic and a synthesis that would not be dependent upon opium alkaloids as starting materials and yet would be commercially feasible.

The objectives of the present invention have been achieved by the provision of the compounds of formula L and by their total synthesis from the readily available starting material 2,7-dimethoxy-1-naphthoic acid.

The compounds of the instant invention have the basic dioxamorphinan nucleus which is numbered and represented by the following plane formula

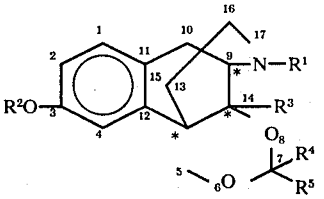

L

Although there are three asymmetric carbons (asterisks) in the dioxamorphinan molecule, only two diastereoisomeric (racemic) forms are possible, because the iminoethano system, attached to position 13 and 9, is geometrically constrained to a cis(1,3-diaxial)-fusion. These racemates can therefore differ only in the configuration of carbon 14. The only variable will be the cis and trans relationship of the 14 carbon substituent to the iminoethano system. When in the compounds of the present invention the 14-substituent ($R^3$) is trans to the iminoethano system, we have the 6,8-dioxaisomorphinans. When the $R^3$ substituent is cis to the iminoethano system, we have the 6,8-dioxamorphinans.

The use of a graphic representation of a dioxamorphinan is meant to include the dl racemic mixture and the resolved d and l isomers thereof.

The compounds of the present invention, the 6,8-dioxamorphinans and the 6,8-dioxaisomorphinans, can exist as two optical isomers, the levorotatory and dextrorotatory isomers. The optical isomers can be graphically illustrated as: 6,8-Dioxamorphinan:

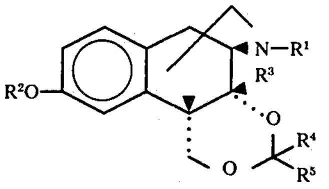

and

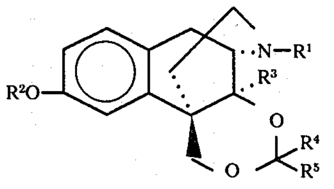

6,8-Dioxaisomorphinan:

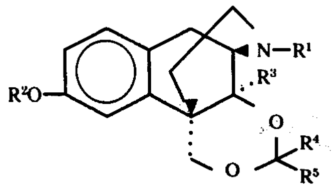

and

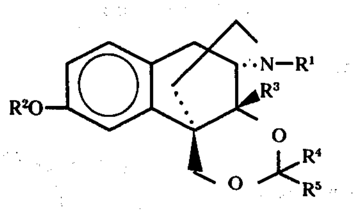

The present invention embodies all of the isomers including the optical isomers in their resolved form.

The optical isomers can be separated and isolated by fractional crystallization of the diastereoisomeric salts formed, for instance, with d- or l- tartaric acid or D-(+)-α-bromocamphor sulfonic acid. The levorotatory isomers of the compounds of the present invention are the most preferred embodiments. Other acids commonly used for resolution can be employed.

For the purpose of this disclosure, the term "(lower)" is applied to a hydrocarbon containing radical consisting of 1 to 6 carbon atoms, e.g. methyl, ethoxy, vinyl, ethinyl, etc. The term "(lower)alkanoyl" is an alkanoyl radical of 2 to 6 carbon atoms, e.g., acetyl, propionyl, isobutyryl, etc. The term "pharmaceutically acceptable acid addition salt" is defined to include all those inorganic an organic acid salts of the compounds of the instant invention, which salts are commonly used to produce nontoxic salts of medicinal agents containing amine functions. Illustrative examples would be those salts formed by mixing the compounds of formula L with hydrochloric, sulfuric, nitric, phosphoric, phosphorous, hydrobromic, maleic, malic, ascorbic, citric, tartaric, pamoic, lauric, stearic, palmitic, oleic, myristic, lauryl sulfonic, napthalenesufonic, linoleic or linolenic acid, fumaric, and the like.

The compounds of the instant invention are prepared by a total synthesis comprising multiple steps. Suprisingly, the synthesis is efficient and appears commerically feasible. The process is outlined in the following charts.

CHART I

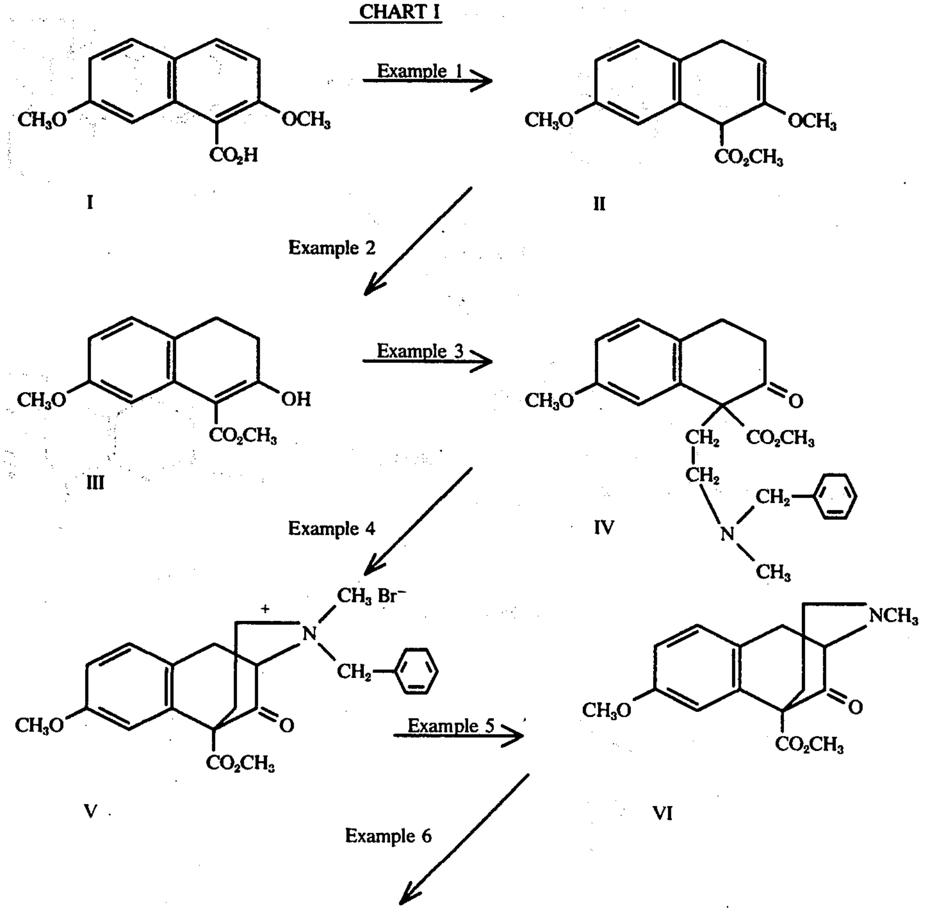

-continued
CHART I
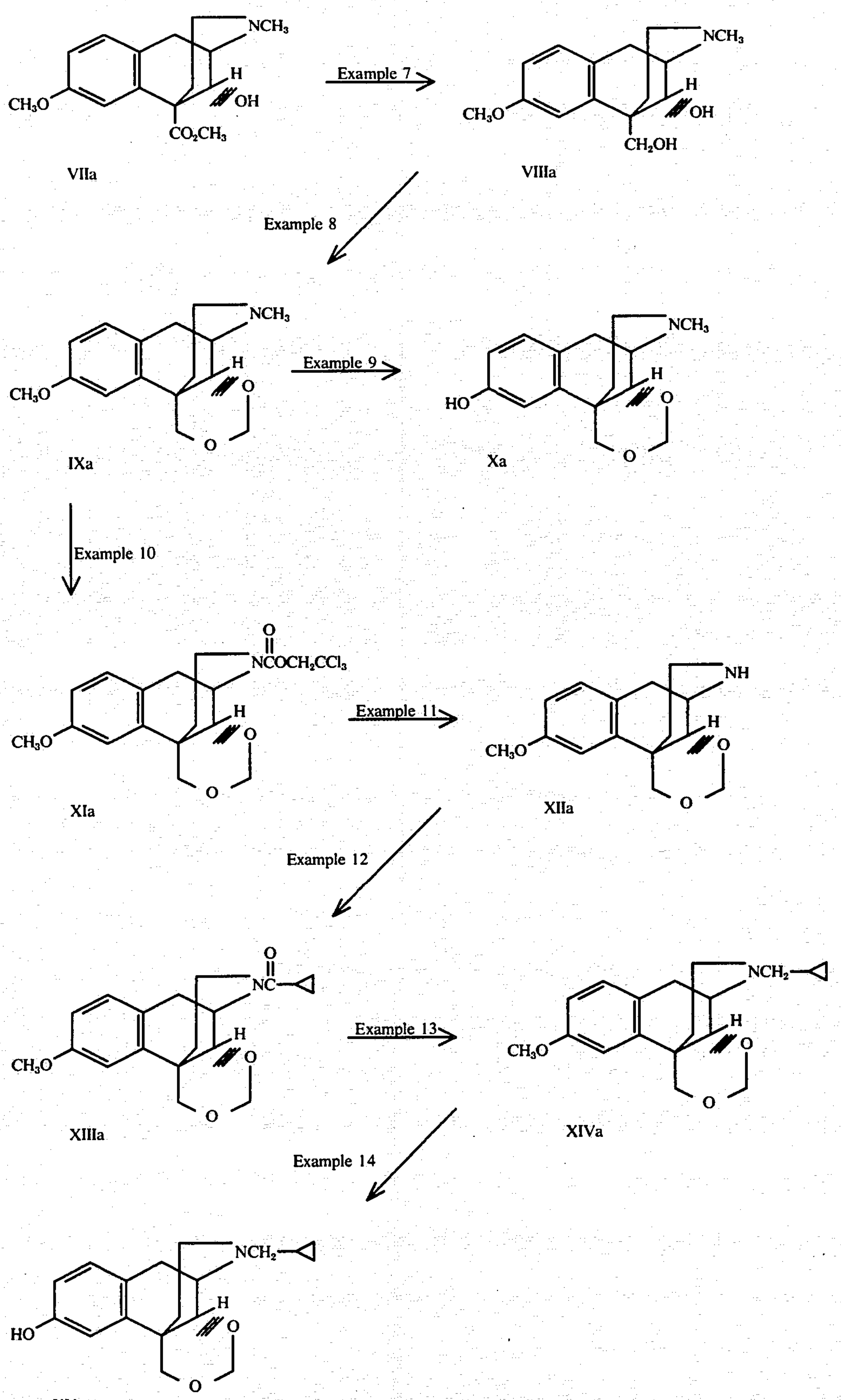
VIIa
VIIIa
IXa
Xa
XIa
XIIa
XIIIa
XIVa
XVa

-continued
CHART I
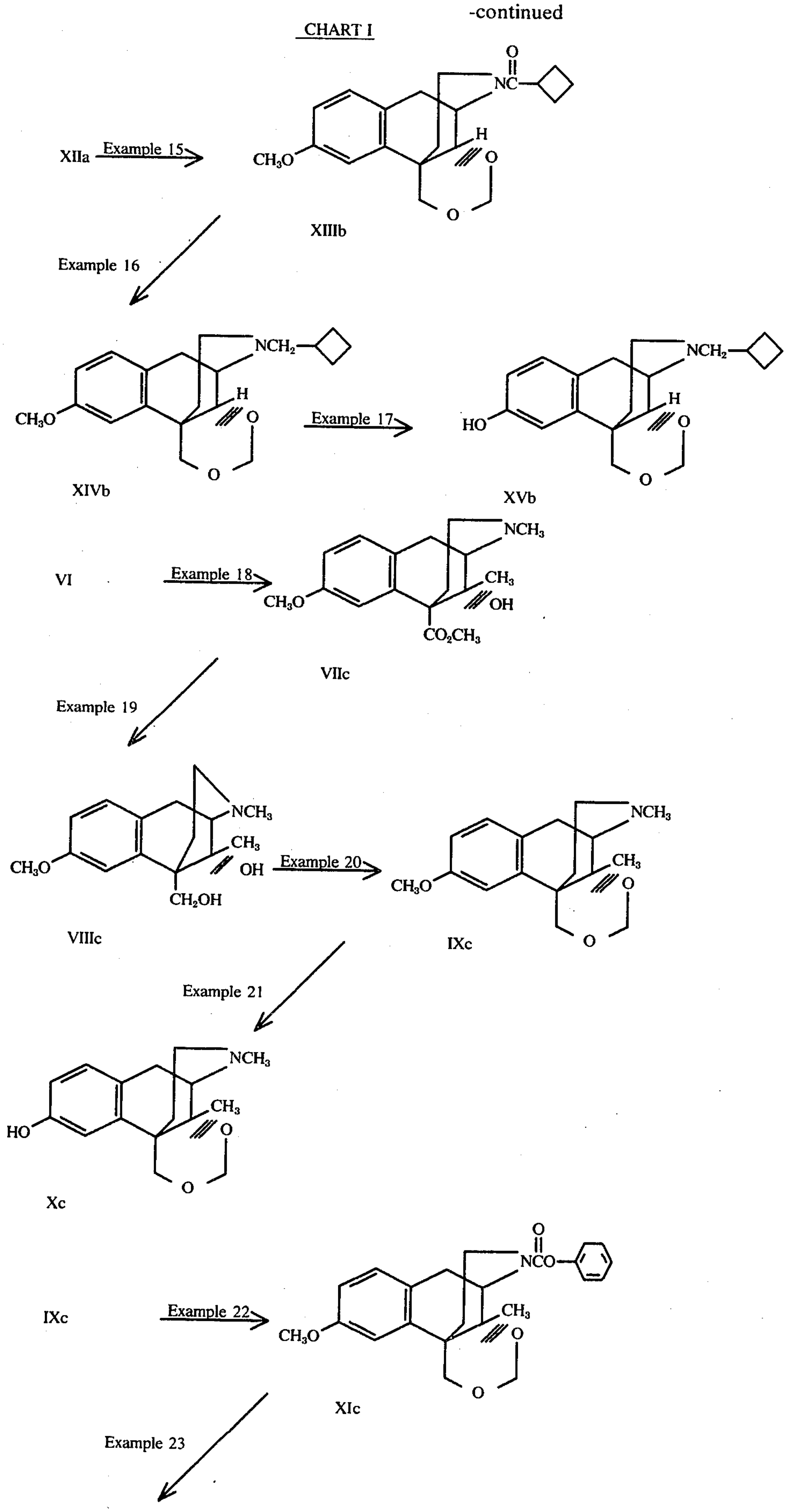
XIIa XIIIb XIVb XVb VI VIIc VIIIc IXc Xc IXc XIc

-continued
CHART I
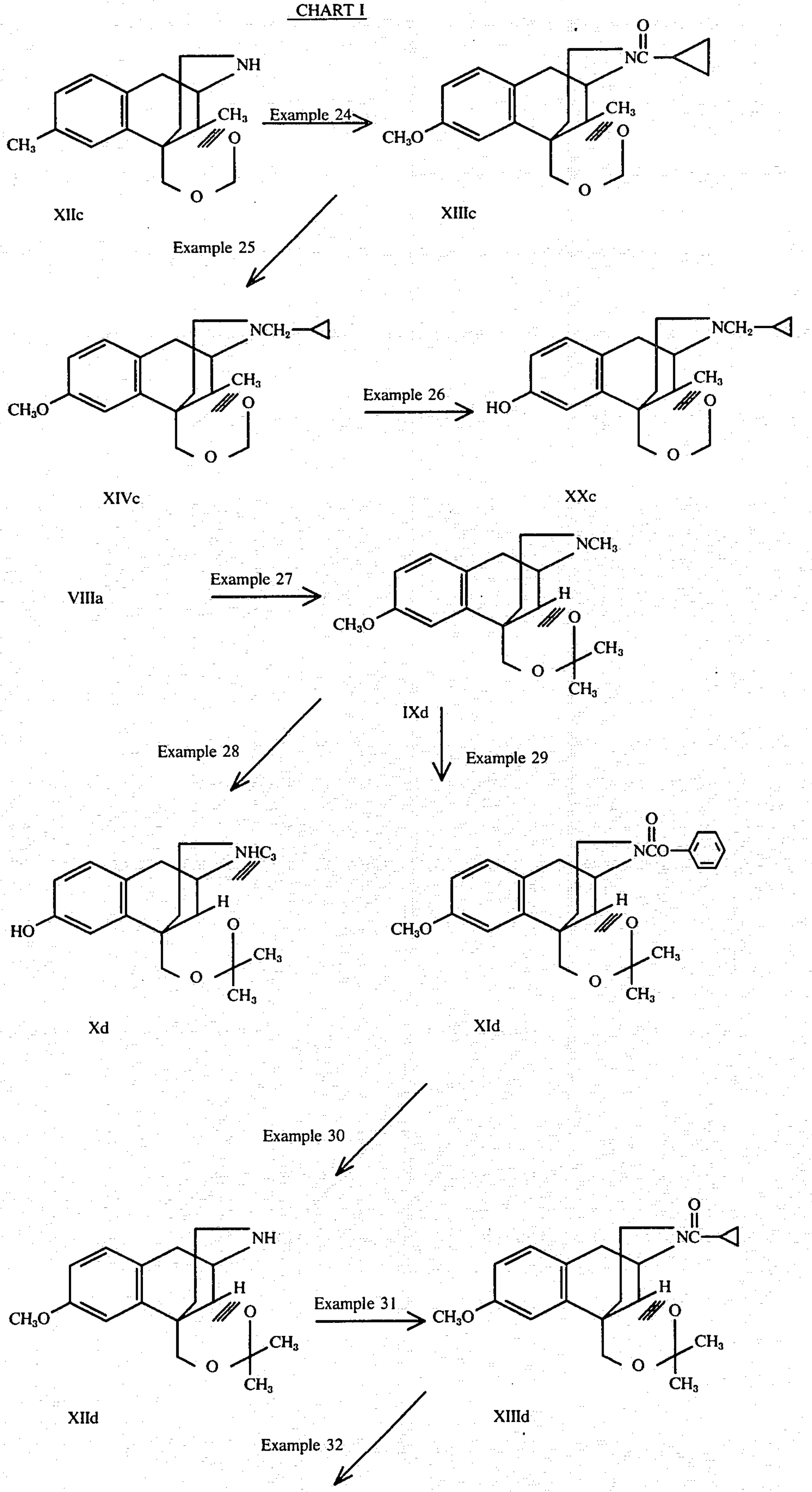
XIIc XIIIc
XIVc XXc
VIIIa IXd
Xd XId
XIId XIIId

-continued

CHART I

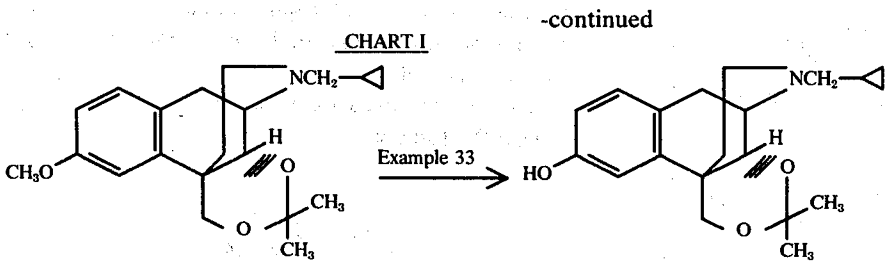

XIVd XVd

A preferred embodiment of the present invention is the compounds having the formula

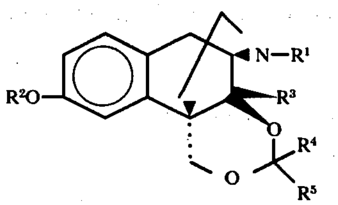

L wherein $R^1$ is selected from the group comprising H,

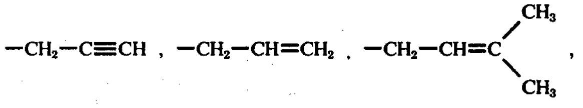

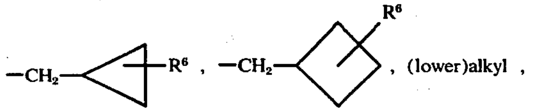

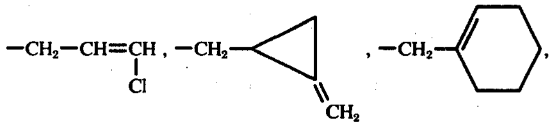

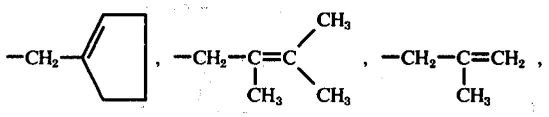

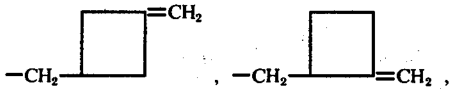

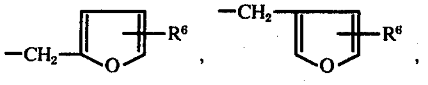

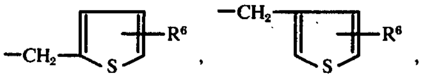

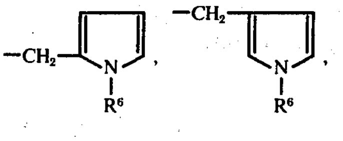

and (lower)alkenyl in which $R^6$ is H or $CH_3$, $R^2$ is selected from the group comprising H, (lower)alkyl,

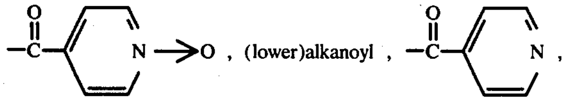

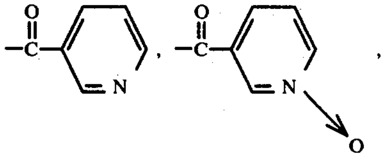

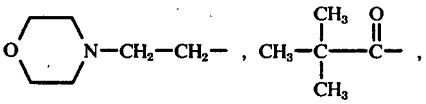

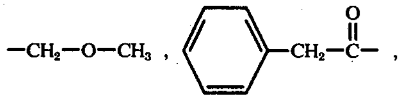

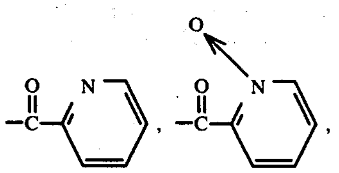

and cinnamoyl, $R^3$ is H or (lower)alkyl and $R^4$ and $R^5$ are alike or different and each is H, (lower)alkyl or trifluoromethyl, or when $R^4$ and $R^5$ are taken together they are a carbonyl or a spirocycloalkyl of 3 to 7 carbon atoms; or a pharmaceutically acceptable acid addition salt thereof.

A preferred embodiment of the present invention is the compounds having the formula

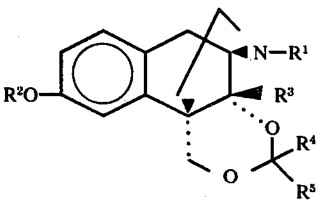

XL wherein $R^1$ is selected from the group comprising H,

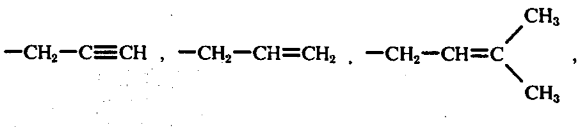

-continued

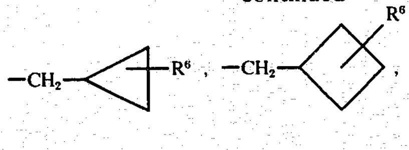

, (lower)alkyl ,

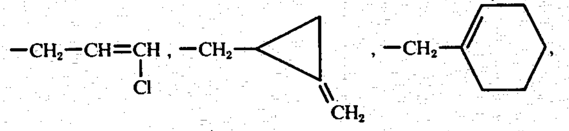

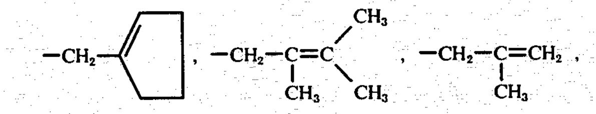

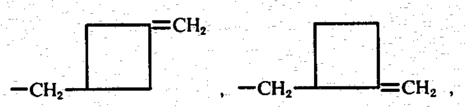

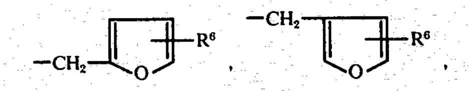

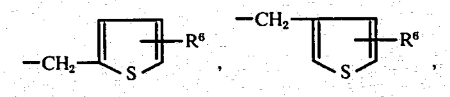

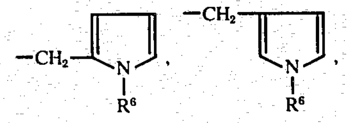

and (lower)alkenyl in which $R^6$ is H or $CH_3$, $R^2$ is selected from the group comprising H, (lower)alkyl,

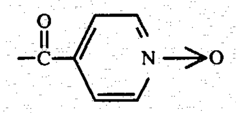

, (lower)alkanoyl ,

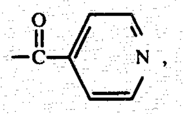

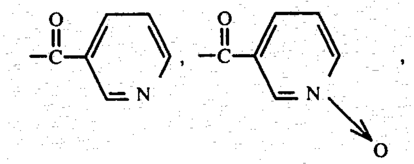

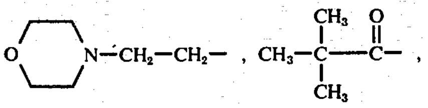

$-CH_2-O-CH_3$ ,

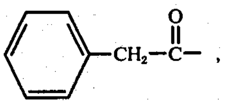

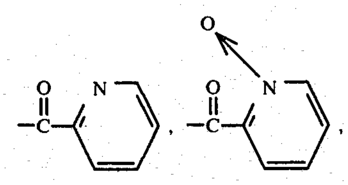

and cinnamoyl, $R^3$ is H or (lower)alkyl and $R^4$ and $R^5$ are alike or different and each is H, (lower)alkyl or trifluoromethyl, or when $R^4$ and $R^5$ are taken together they are a carbonyl or a spirocycloalkyl of 3 to 7 carbon atoms; or a pharmaceutically acceptable acid addition salt thereof.

Another preferred embodiment is the compounds having the formula

XL

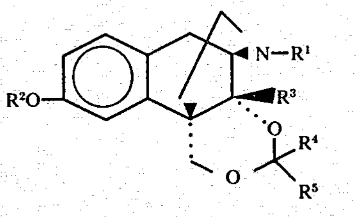

wherein $R^1$ is selected from the group comprising H,

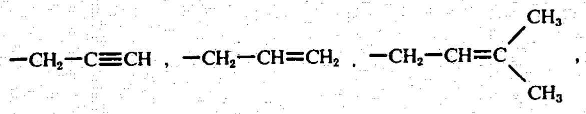

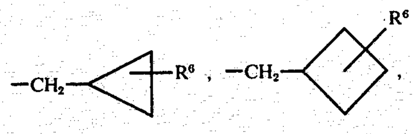

, (lower)alkyl ,

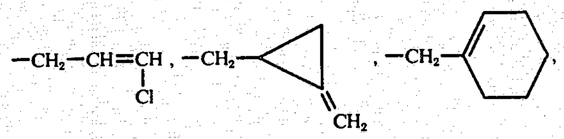

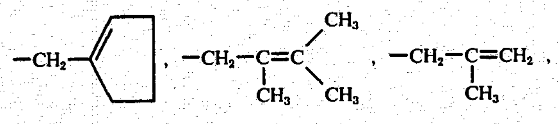

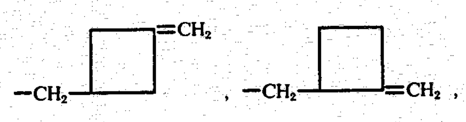

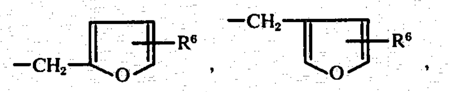

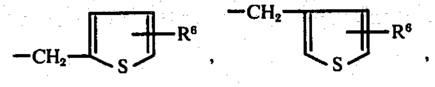

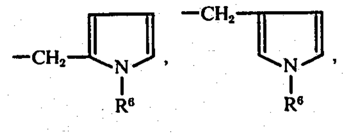

and (lower)alkenyl in which $R^6$ is H or $CH_3$, $R^2$ is selected from the group comprising H, (lower)alkyl,

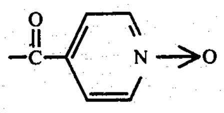

, (lower)alkanoyl ,

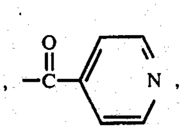

-continued

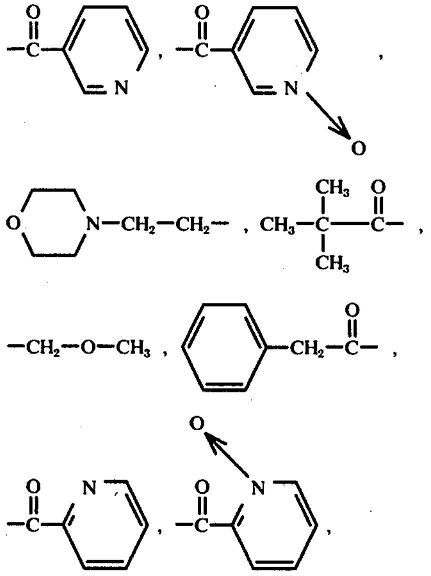

$R^3$ is H, methyl, or ethyl and $R^4$ and $R^5$ are alike or different and each is H, methyl, ethyl, trifluoromethyl or when $R^4$ and $R^5$ are taken together they represent a carbonyl function or a spirocycloalkyl of 3 to 7 carbon atoms; or a pharmaceutically acceptable acid addition salt thereof.

A more preferred embodiment is the compounds of the formula XL wherein $R^1$ is H, $-CH_3$, $-CH_2-CH=CH_2$,

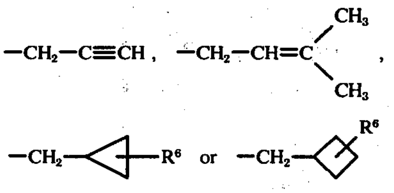

in which $R^6$ is H or $CH_3$, $R^2$ is H, $CH_3$,

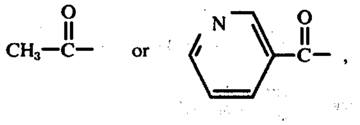

$R^3$ is H or $CH_3$, $R^4$ and $R^5$ are alike or different and each is H, $CH_3$ or $CF_3$, or when taken together $R^4$ and $R^5$ are a spirocycloalkyl group of 3 to 7 carbon atoms; or a pharmaceutically acceptable acid addition salt thereof.

Another more preferred embodiment is the compounds of formula XL wherein $R^1$ is

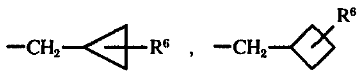

or

H, $R^2$ is H or $CH_3$, $R^3$ is H or $CH_3$, $R^6$ is H or $CH_3$, $R^4$ and $R^5$ are H, $CH_3$ or $CF_3$; or a pharmaceutically acceptable acid addition salt thereof.

Most preferred embodiments are:

1. The compound of formula XL wherein $R^1$ is cyclopropylmethyl, $R^2$ is H or $CH_3$, $R^3$ is H or $CH_3$, and $R^4$ and $R^5$ are H or $CH_3$; or the hydrochloride or tartrate salt thereof.
2. The compound of formula XL wherein $R^1$ is cyclobutylmethyl, $R^2$ is H or $CH_3$, $R^3$ is H or $CH_3$, and $R^4$ and $R^5$ are H or $CH_3$; or the hydrochloride or tartrate salt thereof.
3. The compound of formula XL wherein $R^1$ is cyclobutylmethyl or cyclopropylmethyl, $R^2$ is H or $CH_3$, $R^3$ is H or $CH_3$, and $R^4$ and $R^5$ taken together are carbonyl; or the hydrochloride or tartrate salt thereof.
4. The essentially pure dextrorotatory or levorotatory isomers of the compounds of formula XL.
5. The compound of formula XL wherein $R^1$ is cyclobutylmethyl or cyclopropylmethyl, $R^2$ is H or $CH_3$, $R^3$ is H or $CH_3$, and $R^4$ and $R^5$ are $CF_3$; or the hydrochloride or tartrate salt thereof.
6. The compound of formula XL wherein $R^1$ is cyclopropylmethyl, $R^2$ is H, $R^3$ is H, and $R^4$ and $R^5$ are methyl; or the hydrochloride or tartrate salt thereof.
7. The compound of formula XL wherein $R^1$ is cyclopropylmethyl, $R^2$ is $CH_3$, $R^3$ is H and $R^4$ and $R^5$ are $CH_3$, or the hydrochloride or tartrate salt thereof.
8. The compound of formula XL wherein $R^1$ is cyclopropylmethyl, $R^2$ is H or $CH_3$, $R^3$ is H and $R^4$ and $R^5$ are H; or the hydrochloride or tartrate salt thereof.
9. The compound of formula XL wherein $R^1$ is H, $R^2$ is (lower)alkyl, $R^3$ is H, $CH_3$ or $C_2H_5$, and $R^4$ and $R^5$ are alike or different and each is H, (lower)alkyl or $CF_3$; or when taken together $R^4$ and $R^5$ are carbonyl or a spirocycloalkyl group of 3 to 7 carbon atoms; or an acid addition salt thereof.
10. The levorotatory isomer of the compound of formula XL wherein $R^1$ is cyclopropylmethyl and $R^2$, $R^3$, $R^4$ and $R^5$ are hydrogen; or the hydrochloride, tartrate or fumarate salt thereof.
11. The levorotatory isomer of the compound of the formula XL wherein $R^1$ is cyclopropylmethyl, $R^2$, $R^4$ and $R^5$ are hydrogen and $R^3$ is methyl; or the hydrochloride, tartrate or fumarate salt thereof.

A preferred embodiment of the present invention is the process of preparing compounds having the formula

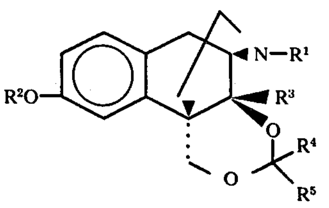

L wherein $R^1$ is selected from the group comprising $-CH_2-C\equiv CH$, $-CH_2-CH=CH_2$, -continued

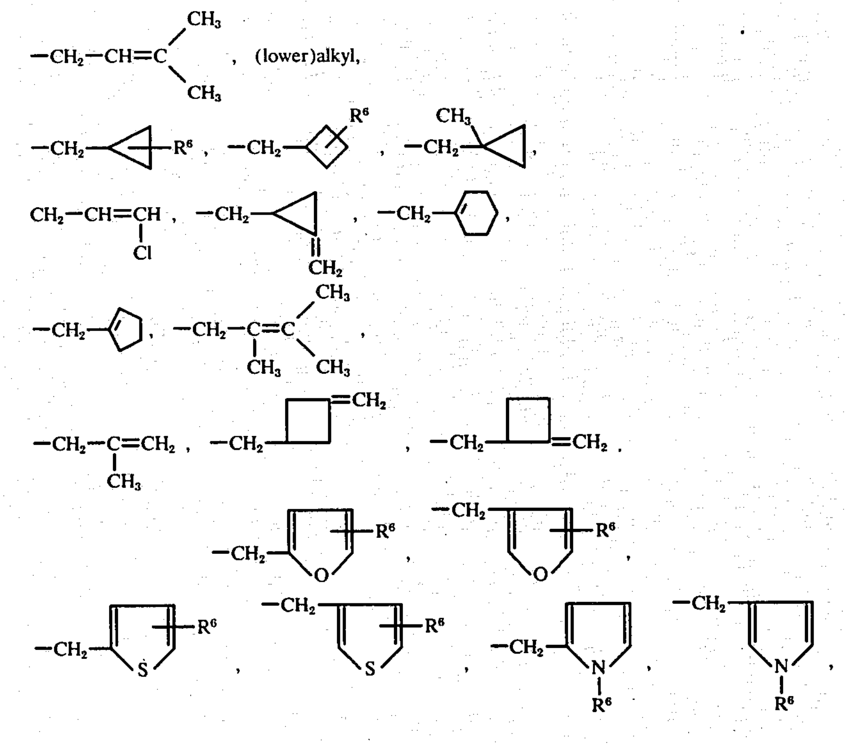

, (lower)alkyl, and (lower)alkenyl in which $R^6$ is H or $CH_3$, $R^3$ is H or (lower)alkyl, $R^2$ is H or (lower)alkyl, and $R^4$ and $R^5$ are alike or different and each is H, (lower)alkyl or $CF_3$, or $R^4$ and $R^5$ when taken together are carbonyl or a spirocycloalkyl of 3 to 7 carbon atoms; which process comprises the consecutive steps of A. treating the compound having the formula

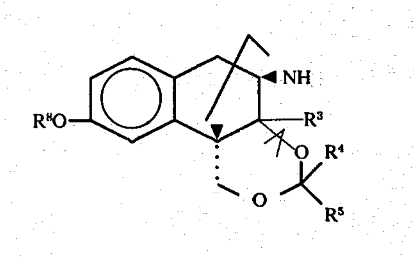

LIII in which $R^8$ is (lower)alkyl and $R^3$, $R^4$ and $R^5$ as defined above, with an alkylating or acylating agent having the formula

X - (Z) - W in which W is a radical selected from the group comprising

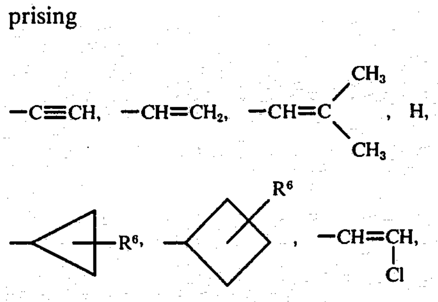

, H, (lower)alkyl

-continued

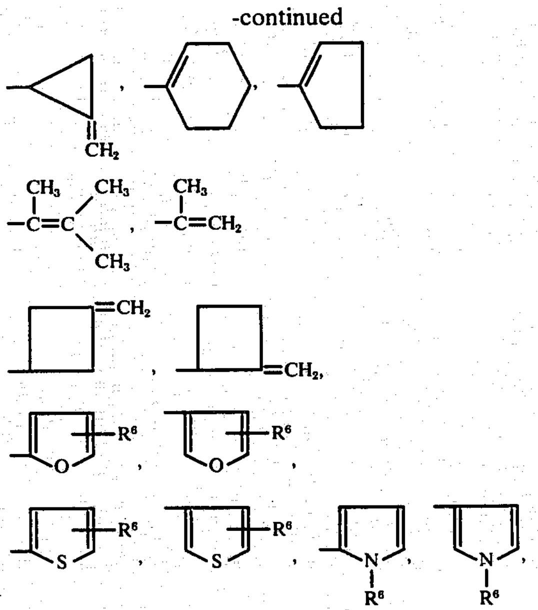

and $C_{2-6}$ alkenyl in which $R^6$ is H or $CH_3$, Z is carbonyl

or $-CH_2-$ and X is chloro, bromo, or iodo, in an inert organic solvent in the presence of an appropriate base to produce the compound having the formula

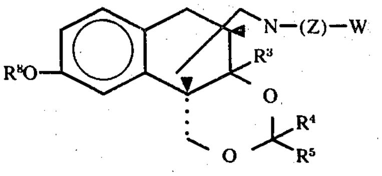

LIV in which $R^3$, Z, W, $R^8$, $R^4$ and $R^5$ are as defined above; and when Z is carbonyl $$(-\overset{O}{\overset{\|}{C}}-)$$

B. treating compound XLIV with lithium aluminum hydride, in an inert organic solvent, to produce the compound having the formula

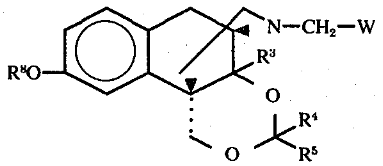

LV in which $R^8$, W, $R^3$, $R^4$ and $R^5$ are as defined above; and when desired C. cleaving the ether function of compound LIV or LV by treatment with an agent selected from the group comprising $NaS\text{-}C_2H_5$, hydrobromic acid, boron tribromide or pyridine hydrochloride.

Another preferred embodiment of the present invention is the process of preparing compounds having the formula

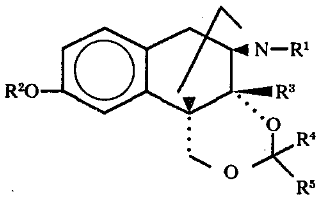

XL wherein $R^1$ is selected from the group comprising $-CH_2-C\equiv CH$ , $-CH_2-CH=CH_2$ , 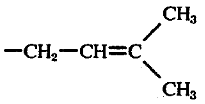 ,

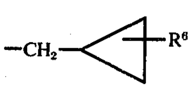 , 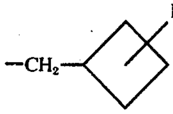 , (lower)alkyl ,

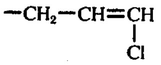 , 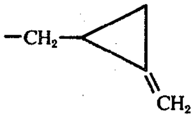 , 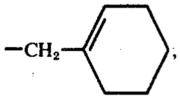;

-continued

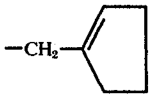 , 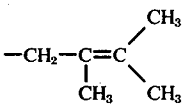 , 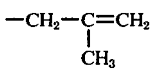 ,

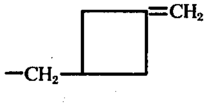 , 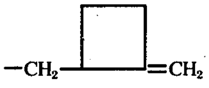 ,

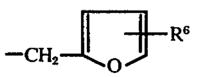 , 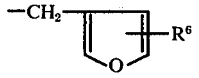 ,

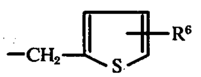 , 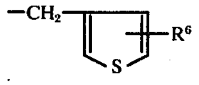 ,

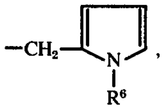 , 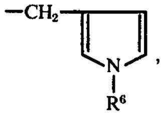 , and (lower)alkenyl in which $R^6$ is H or $CH_3$, $R^3$ is H or (lower)alkyl, $R^2$ is H or (lower)alkyl, and $R^4$ and $R^5$ are alike or different and each is H, (lower)alkyl or $CF_3$, or $R^4$ and $R^5$ when taken together are carbonyl or spirocycloalkyl of 3 to 7 carbon atoms; which process comprises the consecutive steps of A. treating the compound having the formula

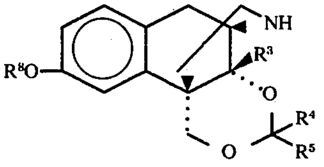

XLIII in which $R^8$ is (lower)alkyl and $R^3$, $R^4$ and $R^5$ as defined above, with an alkylating or acylating agent having the formula

X - (Z) - W in which W is a radical selected from the group comprising $-C\equiv CH$, $-CH=CH_2$, 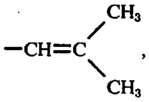 , H, (lower)alkyl

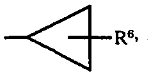, 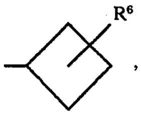 , 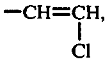,

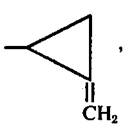 , 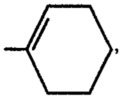, 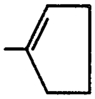

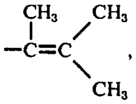 , 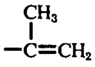

-continued

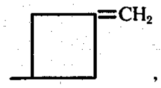 , 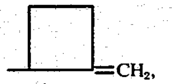

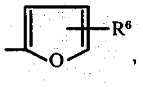 , 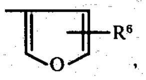 ,

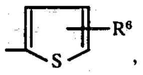 , 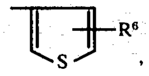 , 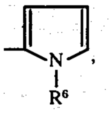 , 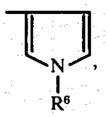

and $C_{2-6}$ alkenyl in which $R^6$ is H or $CH_3$, Z is carbonyl

or $-CH_2-$ and X is chloro, bromo, or iodo, in an inert organic solvent in the presence of an appropriate base to produce the compound having the formula

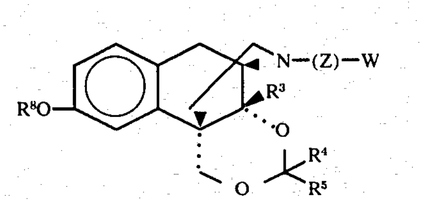

XLIV in which $R^3$, Z, W, $R^8$, $R^4$ and $R^5$ are as defined above; and when Z is carbonyl

B. treating compound XLIV with lithium aluminum hydride, in an inert organic solvent, to produce the compound having the formula

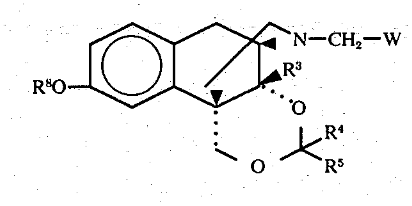

XLV in which $R^8$, W, $R^3$, $R^4$ and $R^5$ are as defined above; and when desired C. cleaving the ether function of compound XLIV or XLV by treatment with an agent selected from the group comprising $NaS-C_2H_5$, hydrobromic acid, boron tribromide or pyridine hydrochloride.

For the purpose of this disclosure the term "inert organic solvent" means an organic solvent that does not participate in the reaction to the extent that it emerges unchanges from the reaction. Such solvents are methylene chloride, chloroform, dichloroethane, tetrachloromethane, benzene, toluene, ether, ethyl acetate, xylene, tetrahydrofuran, dioxane, dimethylacetamide, dimethylformamide, and the like when an acid halide is employed. When an alkylation reaction is being performed, the inert solvent used may also include (lower)alkanols such as methanol, ethanol, n-propanol, isopropanol and the like.

The term "appropriate base" includes inorganic salts such as NaOH, KOH, $K_2CO_3$, $Na_2CO_3$, $NaHCO_3$, $KHCO_3$ and the like and those tertiary amines commonly employed as a proton acceptor in acylation reactions. Such amines are tri(lower)alkylamines, e.g. trimethylamine, triethylamine, and the like, pyridine, dimethylaniline, N-methylpiperidine, and the like.

Acceptable inert organic solvents for use in the lithium aluminum hydride reduction step include among others, diethyl ether, dioxane, tetrahydrofuran, benzene, xylene, toluene and the like.

Another preferred embodiment of the present invention is the process for preparing compounds having the formula

XL

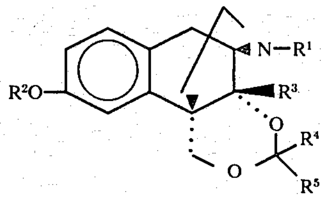

wherein $R^1$ is selected from the group comprising $-CH_2-C\equiv CH$, $-CH_2-CH=CH_2$, 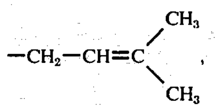 , (lower)alkyl,

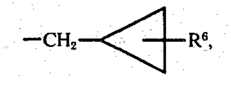 , 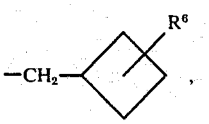 , 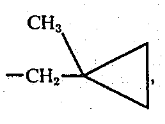 ,

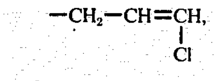 , 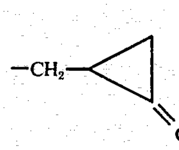 , 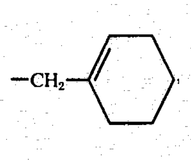 ,

-continued

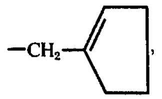

and $C_{3-7}$ alkenyl in which $R^6$ is H or $CH_3$, $R^2$ is H or (lower)alkyl, $R^3$ is H or (lower)alkyl and $R^4$ and $R^5$ are alike or different and each is H, (lower)alkyl or $CF_3$, or when taken together $R^4$ and $R^5$ are carbonyl or spirocycloalkyl of 3 to 7 carbon atoms; which process comprises the consecutive steps of A. treating the compound having the formula

XLIII

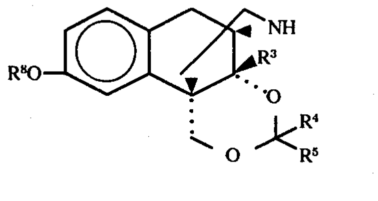

in which $R^8$ is (lower)alkyl and $R^3$, $R^4$ and $R^5$ are as defined above, with an alkylating or acylating agent having the formula

X - (Z) - W in which W is a radical selected from the group comprising

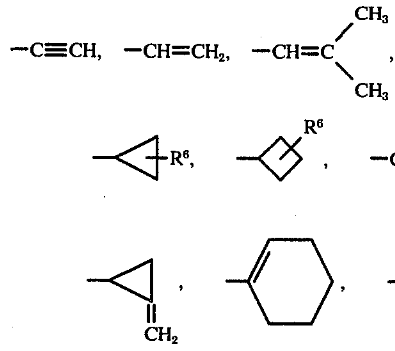

, H, (lower)alkyl and $C_{2-6}$ alkenyl in which $R^6$ is H or $CH_3$, Z is carbonyl

or $-CH_2-$ and X is chloro, bromo or iodo, in an inert organic solvent in the presence of an appropriate base to produce the compound having the formula

XLIV

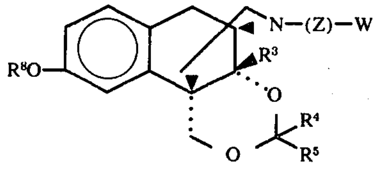

in which $R^3$, Z, W, $R^8$, $R^4$ and $R^5$ are as defined above; and when Z is carbonyl

B. treating compound XLIV with lithium aluminum hydride, in an inert organic solvent, to produce the compound having the formula

XLV

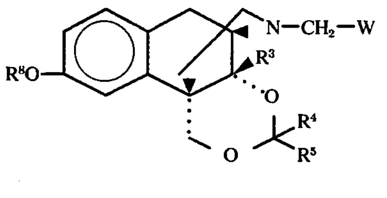

in which $R^8$, W, $R^3$, $R^4$ and $R^5$ are as defined above; and when desired C. cleaving the ether function of compound XLIV or XLV by treatment with an agent selected from the group comprising NaS-$C_2H_5$, hydrobromic acid, boron tribromide or pyridine hydrochloride.

A further preferred embodiment of the present invention is the compounds having the formula

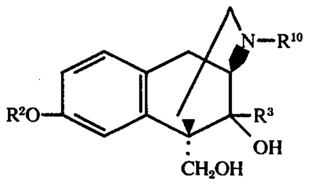

in which $R^{10}$

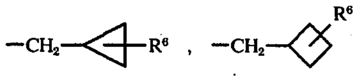

(lower)alkyl, (lower)alkanoyl,

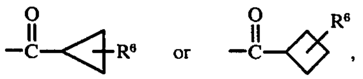

$R^2$ and $R^3$ are H or (lower)alkyl, and $R^6$ is H or $CH_3$; or an acid addition salt thereof.

Another preferred embodiment of the present invention is the compounds having the formula

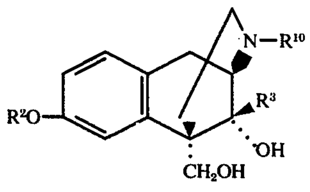

in which $R^{10}$ is

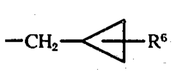 , 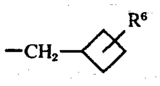

(lower)alkyl, (lower)alkanoyl,

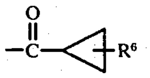 or 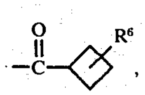 , $R^2$ and $R^3$ are H or (lower)alkyl, and $R^6$ is H or $CH_3$; or an acid addition salt thereof.

Another preferred embodiment of the present invention is the compounds having the formula

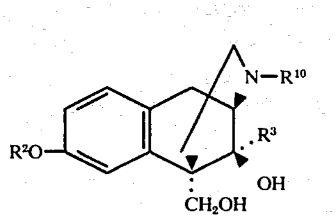

in which $R^{10}$ is

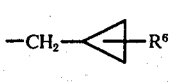 , 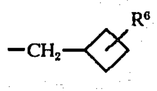

(lower)alkyl, (lower)alkanoyl,

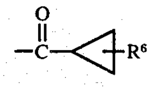 or 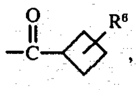 , $R^2$ and $R^3$ are H or (lower)alkyl, and $R^6$ is H or methyl; or an acid addition salt thereof.

All of the compounds of the preferred embodiments herein are novel and valuable for their properties as analgesic and/or narcotic antagonist agents, or as intermediates in the preparation of compounds having these biological acitivities.

In particular, the compounds having the formula XIV and XV are those which possess the most desirable properties; i.e., analgesic and/or narcotic antagonist properties. Some of these compounds also possess antitussive activity, a property generally inherent with an analgetic activity in similar series.

It is well known in the narcotic analgesic prior art that it is possible for some compounds to possess both agonist and antagonist properties. An agonist is a compound that imitates a narcotic analgesic and possesses analgetic qualities. An antagonist is a compound that counteracts the analgetic and euphoric properties of a narcotic analgetic. It is possible for a compound to have both properties. A good example of such a compound is cyclazocine.

In vivo testing was conducted on many of the compounds of the instant invention as illustrated in Table I, to determine their agonist and/or antagonist properties.

Table I represents the results of the experiments. The figures reported are the number of milligrams /kilogram of body weight of compound that produced an agonist or antagonist effect in 50% of the mice and rats so tested ($ED_{50}$).

Table I

| | $ED_{50}$ (mg./kg. s.c.) | | |
|---|---|---|---|
| | Agonist Activity | Antagonist Activity | |
| Test Compound | Phenylquinone Writhing[1] Mouse s.c. | Oxymorphone[2] Straub Tail | Morphine Antagonism[3] Rat Tail Flick |
| IXa | ~5 | >20 | N.D.[4] |
| Xa | 0.30 | >40 | N.D. |
| XIIa | 7.4 | >20 | N.D. |
| IXd | 0.63 | >40 | N.D. |
| Xd | 0.08 | >40 | N.D. |
| IXc | 0.31 | >40 | N.D. |
| Xc | 0.04 | ~40 | N.D. |
| XIIc | 2.0 | ~30 | N.D. |
| XIVa | 0.30 | ~15 | N.D. |
| XVa | 0.02 | 0.30 | 0.12 |
| XIVb | 2 | >40 | N.D. |
| XVb | 0.14 | ~15 | ~9 |
| XIVd | 0.29 | ~30 | N.D. |
| XVd | 0.009 | 0.16 | 0.096 |
| XIVe | 6.1 | >40 | N.D. |
| XVe | 0.04 | ~15 | N.D. |
| XIVc | ~5 | >40 | N.D. |
| XVc | 0.064 | 0.63 | 0.10 |
| (−)XVd | 0.005 | 0.09 | 0.032 |
| (+)-XVd | >10 | >40 | N.D. |
| (−)-XIVd | 0.066 | 5 | 1.19 |
| (+)-XIVd | >40 | >40 | N.D. |

All the compounds were testes as salts, but the weights reported in mg./kg. are corrected and reported in terms of the free base.

[1]A 50 percent reduction in number of phenylquinone induced writhings (Siegmund, E.A. et al., Proc. Soc. Biol. & Med. 95, 729; 1957).

[2]Antagonism of Straub Tail induced by oxymorphone (2 mg./kg. s.c.) in 50 percent of mice.

[3]A 50 precent reduction of analgesic effect induced by morphine (15 mg./kg. s.c.) as measured by the rat tail flick procedure (Harris, L.S. and Pierson, A.K., J. Pharmacol. & Expt. Therap., 143, 141; 1964). [4]N.D. - Not done.

It is apparent from the testing results that all of the compounds exhibited some degree of agonist or antagonist activity. Outstanding among the compounds, however, are the compounds designated XIVa, XVa, XVb, XIVd, XVd, XVe, XVc, (-)-XVd, and (-)-XIVd.

On the basis of the test results in mice and rats, and because it is known that there is a direct correlation between activity in rodents and man, it is anticipated that these compounds will possess significant and substantial activity in man in the dosage range of about 0.25 to 10 mg. parenterally three to four times a day. It is likewise anticipated that the compounds are orally active.

DESCRIPTION OF THE PREFERRED EMBODIMENTS

EXAMPLE 1

Methyl 2,7-dimethoxy-1,4-dihydro-1-naphthoate (II)

A solution of 2,7-dimethoxy-1-naphthoic acid (I) (0.1 mole) in 150 ml. ether and 600 ml. liquid ammonia was treated with 1.73 g. lithium wire in small portions with stirring under argon. This was allowed to reflux (−33° C.) for 1½ hours. Ammonium chloride was added to quench the reaction and the ammonia was allowed to evaporate. The residue was taken up in water and washed with ether. The aqueos layer was acidified with 6 N hydrochloric acid and quickly extracted three times with ether. The ether extracts were washed with saturated sodium chloride; and then treated with an ethereal solution of excess diazomethane (prepared from 20.6 g. N-methyl-N-nitrosourea).[1] After ½ hr., acetic acid was added to destroy the excess diazomethane. The solution was washed with dilute sodium carbonate, dried ($MgSO_4$), and concentrated. The residue was crystallized from methanol; mp 90°–91° C.

Anal. Calcd. for $C_{14}H_{16}O_4$; C, 67.73; H, 6.50.

Found: C, 67.70; H, 6.61.

1. Diazomethane preparation: F. Arndt., Org. Syn., Coll. Vol., 2, 461 (1943)

EXAMPLE 2

Methyl 2-hydroxy-7-methoxy-3,4-dihydro-1-naphthoate (III)

A mixture of II (0.124 mole), oxalic acid (0.124 mole), 400 ml. methanol and 120 ml. water was warmed until solution occurred. This solution was then stirred at 20° C. for 18 hours. The resultant mixture was warmed again to solution and then concentrated. The residue was treated with dilute potassium carbonate and extracted with methylene chloride. The extracts were dried ($MgSO_4$), filtered and concentrated to give III (~100%). Two recrystallizations of a small sample from methanol gave an analytical sample; mp 48.0°–48.5° C.

Anal. Calcd. for $C_{13}H_{14}O_4$; C, 66.65; H, 6.02.

Found: C, 66.88; H, 6.01.

EXAMPLE 3

1-(2′-Benzylmethylaminoethyl)-1-carbomethoxy-7-methoxy-3,4-dihydro-2(1H) naphthalenone (IV)

A solution of III (0.124 m.) in benzene (150 ml). was added to a stirred suspension of sodium hydride (5.95 g. of 50% dispersion in mineral oil) in benzene (200 ml.) under nitrogen. After stirring for ½ hour, a solution of 2-benzylmethylaminoethyl chloride (0.124 m.) in benzene (50 ml.) was added and the mixture heated at reflux for 20 hours. This mixture was cooled and treated with water (200 ml.). The layers were separated and the aqueous layer extracted two times more with benzene. The benzene extracts were washed with saturated sodium chloride solution, combined, dried ($MgSO_4$), filtered and concentrated. The residue was taken up in acetonitrile, washed with n-pentane and concentrated to leave an oil (wt. 44.7 g., ~98%), which was ~99% pure by GLC (gas-liquid chromatography) analysis. This material forms a crystalline hydrogen oxalate salt in methanol; mp 120°–122° C.

Anal. Calcd. for $C_{23}H_{27}NO_4 \cdot C_2H_2O_4$: C, 63.68; H, 6.20; N, 2.97. Found: C, 63.30; H, 6.20; N, 3.11.

EXAMPLE 4

3-Benzyl-6-carbomethoxy-8-methoxy-11-oxo-1,2,3,4,5,6-hexahydro-2,6-methano-3-benzazocine 3-methobromide (V)

A solution of IV hydrobromide (0.13 m.) in 350 ml. acetic acid was treated dropwise with a solution of bromine (0.13 m) in 50 ml. acetic acid. After stirring for ½ hour, the reaction was diluted with 1.5 l. "Skellysolve B" (essentially n-hexane) and cooled. The precipitated residue was separated by decantation and washed with cold "Skellysolve B". The residue was taken up in methylene chloride and treated with dilute ammonium hydroxide until basic. The layers were separated and the aqueous layer extracted two times more with methylene chloride. The combined extracts were dried ($MgSO_4$) and concentrated. The residue was taken up in acetone and allowed to crystallize with stirring. The crystals were collected to give V (69%). The analytical sample was recrystallized from methanol; mp 158°–160° C.

Anal. Calcd. for $C_{23}H_{26}BrNO_4$: C, 60.00; H, 5.72; N, 3.04.

Found: C, 60.27; H, 5.77; N, 3.10.

EXAMPLE 5

6-Carbomethoxy-8-methoxy-3-methyl-11-oxo-1,2,3,4,5,6-hexahydro-2,6-methano-3-benzazocine hydrogen fumarate (VI)

Material V (0.01 m) in 50 ml. acetic acid was hydrogenated at 40 psi using 300 mg 10% palladium on carbon as catalyst until hydrogen uptake stopped (~100% theoretical observed). The catalyst was removed by filtration and the filtrate concentrated. The residue was treated with dilute potassium carbonate and extracted with methylene chloride to give an oil which was converted to a hydrogen fumarate salt in 1-propanol; mp 168°–171° C.

Anal. Calcd. for $C_{16}H_{19}NO_4.C_4H_4O_4$: C, 59.25; H, 5.72; N, 3.46. Found: C, 59.31; H, 5.71; N, 3.42.

EXAMPLE 6

6-Carbomethoxy-11α-hydroxy-8-methoxy-3-methyl-1,2,3,4,5,6-hexahydro-2,6-methano-3-benzazocine hydrogen fumarate (VIIa)

Material VI base (0.05 m) in 200 ml. 90% methanol was hydrogenated at 50 psi using 300 mg. platinum oxide as catalyst until hydrogen uptake ceased (~100% theoretical observed). The catalyst was removed by filtration and the filtrate concentrated to leave a crystalline residue. This material was converted to a hydrogen fumarate salt in 1-propanol; mp 194°–195° C.

Anal. Calcd. for $C_{16}H_{21}NO_4.C_4H_4O_4$: C, 58.96; H, 6.18; N, 3.44. Found: C, 58.65; H, 6.05; N, 3.21.

EXAMPLE 7

11α-Hydroxy-6-hydroxymethyl-8-methoxy-3-methyl-1,2,3,4,5,6-hexahydro-2,6-methano-3- benzazocine hydrogen fumarate (VIIIa)

A solution of VIIa base (0.038 m) in 90 ml. tetrahydrofuran was added to a suspension of 2.9 g. lithium aluminum hydride in 60 ml. tetrahydrofuran. This mixture was heated at reflux for 16 hr. To the cooled reaction mixture was cautiously added 9 ml. saturated sodium sulfate. This mixture was warmed until the solids were white. Removal of the solids by filtration and concentration of the filtrate gave a crystalline solid which was converted to a hydrogen fumarate salt in 1-propanol; mp 187°–188° C.

Anal. Calcd. for $C_{15}H_{21}NO_3$. $C_4H_4O_4$: C, 60.14; H, 6.64; N, 3.69. Found: C, 59.74; H, 6.57; N, 3.59.

EXAMPLE 8

3-Methoxy-17-methyl-6,8-dioxamorphinan (IXa)

A mixture of VIIIa (0.028 m), paraformaldehyde (1.02 g.) and p-toluenesulfonic acid hydrate (6.5 g.) in 200 ml. chloroform (alcohol free) was heated at reflux through a Soxhlet extractor containing 3A molecular sieves for 24 hours. The resultant mixture was cooled and treated with dilute potassium carbonate. Separation of the layers and further extraction with chloroform gave IXa which was recrystallized from ethanol; mp 134°–135° C.

Anal. Calcd. for $C_{16}H_{21}NO_3$: C, 69.79; H, 7.69; N, 5.09. Found: C, 69.49; H, 7.55; N, 4.81.

EXAMPLE 9

3-Hydroxy-17-methyl-6,8-dioxamorphinan fumarate Xa

A mixture of IXa (0.001 m) and sodium thioethoxide (0.016 m) (prepared from sodium hydride and ethyl mercaptan) in 15 ml. dimethyl formamide was heated at reflux for 2 ½ hours. The solvent was removed at reduced pressure. The cooled residue was treated with water, acidified with acetic acid, basified with potassium carbonate and extracted with methylene chloride to give Xa. This material was recrystallized from ethanol and then converted to a fumarate salt in 1-propanol; mp 243°–248° C.

Anal. Calcd. for $(C_{15}H_{19}NO_3)_2 \cdot C_4H_4O_4$: C, 63.93; H, 6.63; N, 4.39. Found: C, 63.77; H, 6.81; N, 4.29.

EXAMPLE 10

3-Methoxy-17-trichloroethoxycarbonyl-6,8-dioxamorphinan (XIa)

A refluxing mixture of IXa (0.0024 m) and potassium carbonate (2g.) in 10 ml. benzene was treated with trichloroethyl chloroformate (1.54 g.) in 10 ml. benzene. After 20 hours at reflux the mixture was washed with water, dried ($MgSO_4$) and concentrated to give crude IXa contaminated with trichloroethyl chloroformate.

EXAMPLE 11

3-Methoxy-6,8-dioxamorphinan hydrogen fumarate (XIIa)

The crude material XIa from example 10 was taken up in 10 ml. methanol and added to stirred mixture of 12 g. zinc dust in 20 ml. methanol. The reaction mixture was heated at reflux for 2 hours. After cooling the zinc was removed by filtration and the filtrate concentrated. The residue was treated with dilute ammonium hydroxide and extracted with methylene chloride to give XIIa as an oil, which was converted to a hydrogen fumarate salt in 1-propanol; mp 223°–226° C.

Anal. Calcd. for $C_{15}H_{19}NO_3 \cdot C_4H_4O_4$: C, 60.47; H, 6.14; N, 3.72. Found: C, 60.80; H, 6.25; N, 3.70.

EXAMPLE 12

17-Cyclopropylcarbonyl-3-methoxy-6,8-dioxamorphinan XIIIa

A solution of XIIa base (0.0053 m) and 2 ml. triethylamine in 20 ml. methylene chloride was treated with a solution of cyclopropylcarbonyl chloride (0.0065 m) in 5 ml. methylene chloride. After stirring for 2 ½ hours, the mixture was washed with dilute hydrochloric acid and the 10% sodium carbonate, dried ($MgSO_4$), and concentrated to give XIIIa as a crystalline solid.

EXAMPLE 13

17-Cyclopropylmethyl-3-methoxy-6,8-dioxamorphinan hydrogen fumarate (XIVa)

The crude material XIIIa from example 12 was dissolved in anhydrous tetrahydrofuran and added to a suspension of lithium aluminum hydride (0.5 g.) in tetrahydrofuran. This mixture was heated at reflux for 16 hours. To the cooled mixture 1.5 ml. saturated sodium sulfate was cautiously added and the mixture warmed until the solids were white. The solids were removed by filtration and the filtrate concentrated. The residue was dissolved in 1-propanol and converted to a hydrogen fumarate salt; m.p. 180°–181° C.

Anal. Calcd. for $C_{19}H_{25}NO_3 \cdot C_4H_4O_4$: C, 64.02; H, 6.77; N, 3.25. Found: C, 63.63; H, 6.81; N, 3.24.

EXAMPLE 14

17-Cyclopropylmethyl-3-hydroxy-6,8-dioxamorphinan XVa

Material XIVa base was O-demethylated using sodium thioethoxide in dimethyl formamide using a similar procedure as used in example 9. Compound XVa was isolated as free base and crystallized from ethanol; mp. 193°–196° C.

Anal. Calcd. for $C_{18}H_{23}NO_3$: C, 71.73; H, 7.69, N, 4.65. Found: C, 71.53; H, 7.43; N, 4.85.

EXAMPLE 15

17-Cyclobutylcarbonyl-3-methoxy-6,8-dioxamorphinan (XIIIb)

Substitution in the procedure of example 12 for the cyclopropyl carbonyl chloride used therein of an equimolar quantity of cyclobutylcarbonyl chloride produced the title product XIIIb.

EXAMPLE 16

17-Cyclobutylmethyl-3-methoxy-6,8-dioxamorphinan XIVb hydrogen fumarate

Substitution in the procedure of example 13 for the compound XIIIa used therein of an equimolar quantity of XIIIb produced the title product XIVb; m.p. 149°–150° C.

Anal. Calcd. for $C_{20}H_{29}NO_3 \cdot C_4H_4O_4$: C, 64.70; H, 7.01; N, 3.14. Found: C, 64.60; H, 6.92; N, 3.26.

EXAMPLE 17

17-Cyclobutylmethyl-3-hydroxy-6,8-dioxamorphinan fumarate (XVb)

Compound XIVb was O-demethylated with sodium thioethioxide in dimethyl formamide as described in example 9 for the O-demethylation of IXa. Compound XVb was isolated as a fumarate salt from 1-propanol; m.p. 231°–237° C.

Anal. Calcd. for $(C_{19}H_{25}NO_3)_2 \cdot C_4H_4O_4$: C, 67.54; H. 7.29; N, 3.75. Found: C, 67.24; H, 7.49; N, 3.64.

EXAMPLE 18

6-Carbomethoxy-11α-hydroxy-3,11β-dimethyl-8-methoxy-1,2,3,4,5,6-hexahydro-2,6-methano-3-benzazocine (VIIc)

A cooled solution of VI base (0.0324 m) in 100 ml. benzene was treated with methyl magnesium chloride (29 ml. of 3.3 M solution in tetrahydrofuran) in 50 ml. benzene. This mixture was heated at reflux for 1 hour then stirred at 20° C. for 18 hours. Dilute ammonium chloride was added and the layers separated. Further extraction with benzene, drying ($MgSO_4$) and concentration of the organic extracts gave VIIc [predominently α-OH isomer (>87%) by GLC analysis]. Recrystallization from methanol gave pure VIIc; m.p. 113–114° C.

Anal. Calcd. for $C_{17}H_{23}NO_4$: C, 66.86; H, 7.59; N, 4.59. Found: C, 67.03; H, 7.53; N, 4.36.

EXAMPLE 19

3,11β-Dimethyl-11α-hydroxy-6-hydroxymethyl-8-methoxy-1,2,3,4,5,6-hexahydro-2,6-methano-3-benzazocine hydrogen fumarate (VIIIC)

Material VIIc (0.023 m) was reduced with lithium aluminium hydride (0.046 m) in tetrahydrofuran (100 ml.) to give compound VIIIc which was crystallized as a hydrogen fumarate salt from 1-propanol; m.p. 197°–202° C.

Anal. Calcd. for $C_{16}H_{23}NO_3.C_4H_4O_4$: C, 61.05; H, 6.92; N, 3.56. Found: C, 61.19; H, 6.98; N, 3.54.

EXAMPLE 20

14β,17-Dimethyl-3-methoxy-6,8-dioxamorphinan (IXc)

Material IXc was prepared from VIIIc base using a procedure similar to that used in example 8. A 48 hour reaction time was used. The crude product was chromatographed on alumina (Woelm neutral alumina grade I) using a 9:1 benzene:ethyl acetate solvent mixture for elution. Crystallization from cyclohexane gave pure IXc; m.p. 109°–110° C.

Anal. Calcd. for $C_{17}H_{23}NO_3$: C, 70.56; H, 8.01 N, 4.84; Found: C, 70.27; H, 7.88; N, 4.69.

EXAMPLE 21

14β,17-Dimethyl-3-hydroxy-6,8-dioxamorphinan fumarate Xc

Material IXc was O-demethylated with sodium thioethioxide in dimethyl formamide using a similar procedure as described in example 9. Compound Xc was purified as a fumarate salt by crystallization from 1-propanol (contains 1 mole 1-propanol solvate); mp 129°–133° C.

Anal. Calcd. for $(C_{16}H_{21}NO_3)_2.C_3H_8O$: C, 64.43; H, 7.49; N, 3.85. Found: C, 64.10; H, 7.66; N, 3.77.

EXAMPLE 22

3-Methoxy-14β-methyl-17-phenoxycarbonyl-6,8-dioxamorphinan (XIc)

A stirred refluxing suspension of IXc (0.0078 m) and 5 g. potassium carbonate in 50 ml. benzene was treated with a solution of phenyl chloroformate (0.023 m) in 15 ml. benzene. This mixture was heated at reflux for 5 days. Water was added to the cooled reaction mixture and the layers separated. Further extraction with benzene followed by drying ($MgSO_4$), filtration and concentration gave XIc as a clear oil.

EXAMPLE 23

3-Methoxy-14β-methyl-6,8-dioxamorphinan hydrogen fumarate XIIc

The crude oil XIc from example 22 was taken up in 2-propanol (300 ml.) and water (70 ml.) and treated with potassium hydroxide (44 g.) and heated at reflux for 40 hours. The 2-propanol was removed at reduced pressure. The residue was diluted with water and extracted with methylene chloride to give XIIc which was converted to a hydrogen fumarate salt in 1-propanol; m.p. 212°–215° C.

Anal. Calcd. for $C_{16}H_{21}NO_3.C_4H_4O_4$: C, 61.37; H, 6.44; N, 3.58. Found: C, 61.38; H, 6.81; N, 3.38.

EXAMPLE 24

17-Cyclopropylcarbonyl-3-methoxy-14β-methyl-6,8-dioxamorphinan (XIIIc)

Substitution in the procedure of example 12 for the compound XIIa used therein of an equimolar quantity of XIIc produced the title compound XIIIc.

EXAMPLE 25

17-Cyclopropylmethyl-3-methoxy-14β-methyl-6,8-dioxamorphinan (XIVc) hydrogen fumarate Substitution in the procedure of example 13 for the compound XIIIa used therein of an equimolar quantity of XIIIc produced the title product as a crystalline salt with 1½ equivalents of fumaric acid from 1-propanol; m.p. 179°–180° C.

Anal. Calcd. for $C_{20}H_{27}NO_3$. 1½ $(C_4H_4O_4)$: C, 62.02; H, 6.62; N, 2.79. Found: C, 62.35; H, 6.83; N, 2.85.

EXAMPLE 26

17-Cyclopropylmethyl-3-hydroxy-14β-methyl-6,8-dioxamorphinan hydrogen fumarate (XVc)

Compound XIVc was O-demethylated with sodium thioethoxide in dimethyl formamide using the same procedure described in example 9. Compound XVc was isolated as a crystalline hydrogen fumarate from 1-propanol; m.p. 203°–206° C.

Anal. Calcd. for $C_{19}H_{25}NO_3.C_4H_4O_4$: C, 64.02; H, 6.77; N, 3.25. Found: C, 64.02; H, 6.78; N, 3.01.

EXAMPLE 27

3-Methoxy-7,7,17-trimethyl-6,8-dioxamorphinan (IXd)

A mixture of VIIIa (0.025 m), 2,2-dimethoxypropane (0.05 m) and p-toluenesulfonic acid hydrate (0.027 m) in 80 ml. chloroform was heated at reflux through a Soxhlet extractor containing 4A molecular sieves for 24 hours. After cooling, solid potassium carbonate was added followed by water. Separation of the layers followed by further extraction of the aqueous layer with chloroform gave IXd which was recrystallized from 2-propanol; m.p. 132°–133° C.

Anal. Calcd. for $C_{18}H_{25}NO_3$: C, 71.25; H, 8.31; N, 4.62. Found: C, 71.28; H, 7.99; N, 4.44.

EXAMPLE 28

3-Hydroxy-7,7,17-trimethyl-6,8-dioxamorphinan (Xd)

Compound IXd was O-demethylated with sodium thioethoxide in dimethyl formamide using the procedure described in example 9. Material Xd was recrystallized from ethanol; m.p. 237°–238° C.

Anal. Calcd. for $C_{17}H_{23}NO_3$: C, 70.56; H, 8.01; N, 4.84. Found: C, 70.55; H, 7.89; N, 4.73.

EXAMPLE 29

7,7-Dimethyl-3-methoxy-17-phenoxycarbonyl-6,8-dioxamorphinan (XId)

A refluxing mixture of IXd (0.054 m) and 70 g. potassium carbonate in 200 ml. benzene was treated with phenyl chloroformate (0.16 m) dissolved in 100 ml. benzene over a period of ½ hour. This mixture was heated at reflux for 20 hours more. The reaction mixture was cooled, washed with water and then with saturated sodium chloride. Drying ($MgSO_4$) and concentration of the organic extract gave crude XId.

EXAMPLE 30

7,7-Dimethyl-3-methoxy-6,8-dioxamorphinan hydrogen fumarate (XIId)

The crude product XId obtained in example 29 was taken up in 600 ml. 2-propanol and treated with 90 g. potassium hydroxide in 140 ml. water and heated at reflux for 2 days. The 2-propanol was removed at reduced pressure. The residue was diluted with water and extracted with methylene chloride. Drying ($MgSO_4$) and concentration of the extracts gave compound XIId which was purified as a crystalline hydrogen fumarate from 1-propanol; m.p. 229°–232° C.

Anal. Calcd. for $C_{17}H_{23}NO_3.C_4H_4O_4$: C, 62.21; H, 6.71; N, 3.46. Found: C, 62.36; H, 6.76; N, 3.85.

EXAMPLE 31

17-Cyclopropylcarbonyl-7,7-dimethyl-3-methoxy-6,8-dioxamorphinan (XIIId)

Substitution in the procedure of example 12 for the compound XIIa used therein of an equimolar quantity of XIId produced the title compound XIIId.

EXAMPLE 32

17-Cyclopropylmethyl-7,7-dimethyl-3-methoxy-6,8-dioxamorphinan hydrogen fumarate (XIVa)

Substitution in the procedure of example 13 for the compound XIIIa used therein of an equimolar quantity of XIIId produced the title compound XIVd which was purified as a crystalline hydrogen fumarate from 1-propanol; m.p. 199°–207° C.

Anal. Calcd. for $C_{21}H_{29}NO_3.C_4H_4O_4$: C, 65.34; H, 7.24; N, 3.05 Found: C, 65.04; H, 7.41; N, 2.95.

EXAMPLE 33

17-Cyclopropylmethyl-7,7-dimethyl-3-hydroxy-6,8-dioxamorphinan hydrogen fumarate (XVd)

Compound XIVd was O-demethylated with sodium thioethoxide in dimethyl formamide using the same procedure described in example 9. Compound XVd was purified as a crystalline hydrogen fumarate from 1-propanol (contains ¼ mole 1-propanol); m.p. > 190° C. decomposition.

Anal. Calcd. for $C_{20}H_{27}NO_3.C_4H_4O_4.¼(C_3H_8O)$: C, 64.45; H, 7.22; N, 3.04. Found: C, 64.55; H7.45; N, 3.05.

EXAMPLE 34

17-Cyclobutylcarbonyl-7,7-dimethyl-3-methoxy-6,8-dioxamorphinan (XIIIe)

Substitution in the procedure of example 12 for the compound XIIa and cyclopropylcarbonyl chloride used therein of equimolar quantities of compound XIId and cyclobutylcarbonyl chloride respectively produced the title compound XIIIe.

EXAMPLE 35

17-Cyclobutylmethyl-7,7-dimethyl-3-methoxy-6,8-dioxamorphinan hydrogen fumarate (XIVe)

Substitution in the procedure of example 13 for the compound XIIIa used therein of an equimolar quantity of XIIIe produced the title compound XIVe which was isolated and purified as crystalline hydrogen fumarate salt from 1-propanol-ethyl acetate (1:1), m.p. 206°–208° C.

Anal. Calcd. for $C_{22}H_{31}NO_3.C_4H_4O_4$: C, 65.94; H, 7.45; N, 2.96. Found: C, 66.01; H, 7.33; N, 3.07.

EXAMPLE 36

17-Cyclobutylmethyl-7,7-dimethyl-3-hydroxy-6,8-dioxamorphinan hydrogen fumarate (XVe)

Compound XVe (base) was O-demethylated with sodium thioethoxide in dimethyl formamide using the procedure described in example 9. Compound XVe was purified as a crystalline hydrogen fumarate from 1-propanol (contains ¼ mole water); m.p. 170°–172° C.

Anal. Calcd. for $C_{21}H_{29}NO_3.C_4H_4O_4.(H_2O)_{1/4}$: C, 64.70; H, 7.28; N, 3.02; $H_2O$, 0.95. Found: C, 64.69; H, 7.31; N, 3.14; $H_2O$, 1.25.

EXAMPLE 37

3-Methoxy-17-methyl-7-oxo-6,8-dioxamorphinan hydrogen fumarate (IXf)

A refluxing solution of VIIIa (base) (0.003 m) in toluene (20 ml.) was treated in portions with 1,1′-carbonyldiimidazole (0.0033 m). This was heated at reflux for 18 hours. The reaction mixture was washed with water, saturated sodium chloride solution, dried ($MgSO_4$), filtered and concentrated. The resultant oil was converted to a crystalline hydrogen fumarate salt in 1-propanol; m.p. 156°–158° C.

Anal. Calcd. for $C_{16}H_{19}NO_4.C_4H_4O_4$: C, 59.25; H, 5.72; N, 3.46. Found: C, 59.00; H, 5.57; N, 3.54.

EXAMPLE 38

3-Cyclopropylmethyl-11α-hydroxymethyl-8-methoxy-1,2,3,4,5,6-hexahydro-2,6-methano-3-benzazocine (VIIIf)

A solution of XIVd (0.02 m) in 210 ml. 80% acetic acid was heated on a steam bath for 4 hours. The reaction mixture was concentrated, treated with dilute potassium carbonate and extracted with methylene chloride. The methylene chloride extracts were dried ($MgSO_4$), filtered and concentrated to give crystalline VIIIf which was recrystallized from absolute ethanol; m.p. 181°–182° C.

Anal. Calcd. for $C_{18}H_{25}NO_3$: C, 71.25; H, 8.31; N, 4.62. Found: C, 71.00; H, 8.23; N, 4.41.

EXAMPLE 39

17-Cyclopropylmethyl-3-methoxy-7-oxo-6,8-dioxamorphinan hydrogen fumarate (XIVf)

Substitution in the procedure of example 37 for the compound VIIIa used therein of an equimolar amount of compound VIIIf produces the title compound XIVf.

EXAMPLE 40

Resolution of 6-carbomethoxy-8-methoxy-3-methyl-11-oxo-1,2,3,4,5,6-hexahydro-2,6-methano-3-benzazocine (VI)

A. (−)-6-Carbomethoxy-8-methoxy-3-methyl-11-oxo-1,2,3,4,5,6-hexahydro-2,6-methano-3-benzazocine (+) hydrogen tartrate [(−)-VI]

A mixture of racemic VI base (15.8 g., 0.054 m) and (+) tartaric acid (8.2 g.; 0.54 m) was taken up in hot methanol and allowed to crystallize while cooling to 20° C. then finally at 0° C. The crystals were collected, washed with cold methanol and dried to give (−)-VI-(+) hydrogen tartrate. Recrystallization from methanol gave (−)-VI- (+)hydrogen tartrate; m.p. 163°–165° C.; $[\alpha]_D^{25}$ −41.1° (c 1.06, 70% methanol-water). The free base: $[\alpha]_D^{25}$ −89.5° (c 1.95, methanol).

Anal. Calcd. for $C_{16}H_{19}NO_4.C_4H_6O_6.(H_2O)_{1/4}$: C, 54.11; H, 5.79; N, 3.13; $H_2O$, 0.96. Found: C, 53.89; H, 5.88; N, 3.47; $H_2O$, 1.04.

B. (+)-6-Carbomethoxy-8-methoxy-3-methyl-11-oxo-1,2,3,4,5,6-hexahydro-2,6-methano-3-benzazocine (−) hydrogen tartrate [(+)-VI]

The mother liquors from step A were concentrated. The residue was converted to free base with dilute sodium carbonate and extraction with methylene chloride. This material (9 g.) was treated with (−) tartaric acid (4.7 g.), taken up in hot methanol and cooled as before for crystallization. The crystals were collected and recrystallized from methanol to give pure (+)-VI-(−)hydrogen tartrate; m.p. 163°–165° C.; $[\alpha]_D^{25}$ +41.8° (c 1.12, 70% methanol-water). The free base: $[\alpha]_D^{25}$ + 89.8° (c 1.75, methanol).

Anal. Calcd. for $C_{16}H_{19}NO_4.C_4H_6O_6.(H_2O)_{1/4}$: C, 54.11; H, 5.79; N, 3.13; $H_2O$, 0.96. Found: C, 53.94; H, 5.90; N, 3.37; $H_2O$, 0.73.

EXAMPLE 41

(−)-6-Carbomethoxy-11α-hydroxy-8-methoxy-3-methyl-1,2,3,4,5,6-hexahydro-2,6-methano-3-benzazocine (+) hydrogen tartrate [(−)-VIIa]

Material (−)-VI (base) was reduced with hydrogen over platinum oxide as described in example 6 for racemic VI. (−)-VII Was purified as a (+) hydrogen tartrate salt; m.p. 171°–172° C., $[\alpha]_{Hg\text{-}36,}$−43.3° (c 1.04, 70% methanol-water). The free base has a rotation of $[\alpha]_D$−31.6° (c 1.05, methanol).

Anal. Calcd. for $C_{16}H_{21}NO_4.C_4H_6O_6$: C, 54.42; H, 6.17; N, 3.17. Found: C, 54.00; H, 6.07; N, 3.21; $H_2O$, 0.17.

EXAMPLE 42

(−)-11α-Hydroxy-6-hydroxymethyl-8-methoxy-3-methyl-1,2,3,4,5,6-hexahydro-2,6-methano-3-benzazocine [(−)-VIII]

Material (−)-VII (base) was reduced with lithium aluminum hydride in tetrahydrofuran in a manner identical to that described in example 7. Compound (−)-VIII was isolated as the free base and recrystallized from methanol; m.p. 160°–161.5° C.; $[\alpha]_D$−54.7° (c 1.02, methanol).

Anal. Calcd. for $C_{15}H_{21}NO_3$: C, 68.41; H, 8.04; N, 5.32. Found: C, 68.64; H, 8.11; N, 5.11.

EXAMPLE 43

(−)-3-Methoxy-7,7,17-trimethyl-6,8-dioxamorphinan [(−)-IXd]

Compound (−)-IXd was prepared from (−)-VIIIa by substitution in the procedure described in example 27. (−)-IXd was purified by recrystallization from acetone; m.p. 165°–166° C.; $[\alpha]_D$−12.0°; $[\alpha]_{Hg\text{-}365}$−81.4° (c 1.25, chloroform).

Anal. Calcd. for $C_{18}H_{25}NO_3$: C, 71.25; H, 8.31; N, 4.62. Found: C, 71.54; H, 8.26; N, 4.35.

EXAMPLE 44

7,7-Dimethyl-3-methoxy-17-phenoxycarbonyl-6,8-dioxamorphinan [(−)-XId]

Substitution in the procedure of example 29 for the compound IXd used therein of an equimolar quantity of (−)-IXd produced the title compound (−)-XId.

EXAMPLE 45

(−)-7,7-Dimethyl-3-methoxy-6,8-dioxamorphinan hydrogen fumarate [(−)-XIId]

Substitution in the procedure of example 30 for the compound XId used therein of an equimolar quantity of (−)-XId produced the title compound (−)-XIId which was isolated as a hydrogen fumarate containing ¼ mole water from 1-propanol; m.p. 205°–217° C., $[\alpha]_{Hg\text{-}365}$−50.1° (c 1.12 methanol).

Anal. calcd. for $C_{17}H_{23}NO_3.C_4H_4O_4.(H_2O)_{1/4}$: C, 61.53; H, 6.79; N, 3.42; $H_2O$, 1.06. Found: C, 61.71; H, 6.58; N, 3.70; $H_2O$, 0.72.

EXAMPLE 46

(−)-17-Cyclopropylcarbonyl-7,7-dimethyl-3-methoxy-6,8-dioxamorphinan [(−)-XIIId]

Substitution in the procedure of example 12 for the compound XIIa used therein of an equimolar quantity of compound (−)-XIId produced the title compound (−)-XIIId.

EXAMPLE 47

(−)-17-Cyclopropylmethyl-7,7-dimethyl-3-methoxy-6,8-dioxamorphinan-(+)-hydrogen tartrate [(−)-XIVd]

Substitution in the procedure of example 13 for the compound XIIIa used therein of an equimolar quantity of (−)-XIIId produced the title compound 30 −)-XIVd which was isolated as a (+)hydrogen tartrate salt from methanol-ethyl acetate; m.p. 169°–170° C.; $[\alpha]_D$−17.4° (c 1.09, methanol). $[\alpha]_{Hg\text{-}365}$−93.5° (c 1.09, methanol).

Anal. calcd. for $C_{21}H_{29}NO_3$. $C_4H_6O_6$: C, 60.84; H, 7.15; N, 2.84. Found: C, 60.63; H, 7.32; N, 2.86.

EXAMPLE 48

(−)-17-Cyclopropylmethyl-7,7-dimethyl-3-hydroxy-6,8-dioxamorphinan (+) tartrate [(−)-XVd]

Compound (−)-XIVd base was O-demethylated with sodium thioethoxide in dimethyl formamide using the procedure described in example 9. compound (−)-XVd was isolated as a (+) tartrate salt from methanol-water; m.p. 206.5°–208° C.; $[\alpha]_D$−34.5° (c 1.23, water).

Anal. calcd. for $(C_{20}H_{27}NO_3)_2.C_6H_6O_6.CH_4O$(methanol): C, 64.28; H, 7.67; N, 3.34. Found: C, 64.19; H, 7.55; N, 3.39.

EXAMPLE 49

17-Cyclopropylmethyl-3-hydroxy-7-oxo-6,8-dioxamorphinan fumarate (XVf)

Sutstitution in the procedure of example 9 for the compound IXa used therein of an equimolar quantity of compound XIVf produces the title compound XVf.

EXAMPLE 50

17-Propargyl-3-methoxy-6,8-dioxamorphinan (XIVg)

A mixture of 1.8 mmole of propargyl bromide, 1.8 mole of compound XIIa and 4.8 mmole of sodium bicarbonate in 5 ml. of dry dimethylformamide (DMF) is stirred overnight at room temperature. The reaction mixture is then diluted with ether and filtered. The filtrate is extracted with 0.05 N HCl, the layers separated and the acidic layer made alkaline with concentrated ammonium hydroxide before extraction with ether. After drying over potassium carbonate, compound XIVg is obtained upon evaporation of the ether in vacuo.

EXAMPLE 51

17-Propargyl-3-hydroxy-6,8-dioxamorphinan hydrogen fumarate (XVg)

Substitution in the procedure of example 9 for the compound IXa used therein of an equimolar quantity of compound XIVg produces the title compound XVg.

EXAMPLE 52

17-Allyl-3-methoxy-6,8-dioxamorphinan (XIVb)

Substitution in the procedure of example 50 for the propargyl bromide used therein of an equimolar quantity of allyl bromide produces compound XIVb.

EXAMPLE 53

17-Allyl-3-hydroxy-6,8-dioxamorphinan (XVb)

Substitution in the procedure of example 9 for the compound IXa used therein of an equimolar quantity of compound XIVb produces the title compound XVb.

EXAMPLE 54

3-Acetoxy-17-cyclopropylmethyl-6,8-dioxamorphinan

To 1 ml. of acetic anhydride is added 0.001 mole of compound XVd and 0.08 g. of pyridine. The resulting solution is refluxed for 1 hour and the solvents evaporated in vacuo. The residue is taken up in ether and washed with dilute ammonium hydroxide and then water. The ether solution is dried over anhydrous sodium sulfate, filtered and evaporated to dryness in vacuo to yield the desired acetate ester.

EXAMPLE 55

17-Cyclopropylmethyl-3-(3′-nicotinoyloxy)-6,8-dioxamorphinan

To a solution of 0.002 mole of compound XVd in 3 ml. of pyridine is added 0.0025 mole of 3-nicotinoyl chloride hydrochloride. The mixture is refluxed for one hour and the solvents evaporated. The residue is partitioned between ether and dilute ammonium hydroxide, the ether layer separated, washed with water, dried over anhydrous sodium sulfate, filtered and evaporated in vacuo to produce the desired nicotinoyl ester.

EXAMPLE 56

17-Cyclopropylmethyl-3-(4′-nicotinoyloxy)-6,8-dioxamorphinan

Substitution in the procedure of example 55 for the 4-nicotinoyl chloride hydrochloride used therein of an equimolar quantity of 4-nicotinoyl chloride produces the desired ester.

EXAMPLE 57

(+)-6-Carbomethoxy-11α-hydroxy-8-methoxy-3-methyl-1.2.3.4.5.6-hexahydro-2,6-methano-3-benzazocine (−) hydrogen tartrate [(+)-VUUa]

Material (+)-VI (base) was reduced with hydrogen over platinum oxide as described in example 6 for racemic VI. (+)-VII was purified at a (−) hydrogen tartrate salt; m.p. 172°–173° C. The free base has a rotation of $[\alpha]_D + 31.9°$ (c 1.13, methanol).

Anal. Calcd. for $C_{16}H_{21}NO_4 \cdot C_4H_6O_6$: C, 54,42; H, 6.17; N, 3.17. Found: C, 54.19; H, 6.10; N, 3.44.

EXAMPLE 58

(+)-11α-Hydroxy-6-hydroxymethyl-8-methoxy-3-methyl-1.2.3.4.5.6-hexahydro-2,6-methano-3-benzazocine [(+)-VIII]

Material (+)-VII (base) was reduced with lithium aluminum hydride in tetrahydrofuan in a manner identical to that described in example 7. Compound (+)-VIII was isolated as the free base and recrystallized from methanol; m.p. 159.5°–160.5° C.; $[\alpha]_D + 54.4°$ (c 1.01, methanol).

Anal. Calcd. for $C_{15}H_{21}NO_3$: C, 68.41; H, 8.04; N, 5.32. Found: C, 68.19; H, 8.13; N, 5.16.

EXAMPLE 59

(+)-3-Methoxy-7.7.17-trimethyl-6,8-dioxamorphinan [(+)-IXd]

Compound (+)-IXd was prepared from (+)-VIIIa by substitution in the procedure described in example 27. (+)-IXd was purified by recrystallization frome acetone; m.p. 161°–162° C.; $[\alpha]_D + 12.0°$; $[\alpha]_{Hg\text{-}365} + 80.9°$ (c 1.25, chloroform).

Anal. Calcd. for $C_{18}H_{25}NO_3$: C, 71.25; H, 8.31; N, 4.62. Found: C, 71.50; H, 8.12; N, 4.26.

EXAMPLE 60

7.7-Dimethyl-3-methoxy-17-phenoxycarbonyl-6,8-dioxamorphinan [(+)-XId]

Substitution in the procedure of example 29 for the compound IXd used therein of an equimolar quantity of (+)-IXd produced the title compound (+)-XId.

EXAMPLE 61

(+)-7,7-Dimethyl-3-methoxy-6,8-dioxamorphinan hydrogen fumarate [(+)-XIId]

Substitution in the procedure of example 30 for the compound XId used therein of an equimolar quantity of (+)-XId produced the title compound (+)-XIId which was isolated as a hydrogen fumarate. The crude product was used as is without further purification.

EXAMPLE 62

(+)-17-Cyclopropylcarbonyl-7,7-dimethyl-3-methoxy-6,8-dioxamorphinan [(+)-XIIId]

Substitution in the procedure of example 12 for the compound XIIa used therein of an equimolar quantity of compound (+)-XIId produced the title compound (+)-XIIId.

EXAMPLE 63

(+)-17-Cyclopropylmethyl-7,7-dimethyl-3-methoxy-6,8-dioxamorphinan-(−)-hydrogen tartrate [(+)-XIVd]

Substitution in the procedure of example 13 for the compound XIIIa used therein of an equimolar quantity of (+)-XIIId produced the title compound (+)-XIVd which was isolated as a (−)hydrogen tartrate salt from methanol-ethyl acetate; m.p. 168°–169° C.; $[\alpha]_{Hg\text{-}365}$ + 93.2° (c 1.24, methanol).

Anal. Calcd. for $C_{21}H_{29}NO_3 \cdot C_4H_6O_6$: C, 60.84; H, 7.15; N, 2.84. Found: C, 60.86; H, 7.02; N, 2.95.

EXAMPLE 64

(+)-17,Cyclopropylmethyl-7,7-dimethyl-3-hydroxy-6,8-dioxamorphinan (−) tartrate [(+)-XVd]

Compound (+)-XIVd base was O-demethylated with sodium thioethoxide in dimethyl formamide using the procedure described in example 9. Compound (+)-XVd was isolated as a (−) tartrate salt from methanol-water; m.p. 207°–209° C.; $[\alpha]_D$+34.2° (c 1.26, water).

Anal. Calcd. for $(C_{20}H_{27}NO_3)_2 \cdot C_6H_6O_6 \cdot CH_4O$(methanol): C, 64.28; H, 7.67; N, 3.34. Found: C, 64.29; H, 7.72; N, 3.38.

EXAMPLE 65

11α-Hydroxy-8-methoxy-3-methyl-6-methylsulfonyloxymethyl-1,2,3,4,5,6-hexahydro-2,6-methano-3-benzazocine hydrogen fumarate (XXV)

A solution of VIIIa base (0.0027 m) in methylene chloride (10 ml.) and triethylamine (0.4 g.) was treated with methane sulfonyl chloride (0.003 m) and stirred for 2 hours. The reaction mixture was washed with water, dried ($MgSO_4$) and concentrated. The residue was purified as a hydrogen fumarate salt from 1-propanol; m.p. 173°–173.5° C.

Anal. Calcd. for $C_{16}H_{23}NO_5S \cdot C_4H_4O_4$: C, 52.50; H, 5.95; N, 3.06. Found: C, 52,35; H, 6.08; N, 3.00.

EXAMPLE 66

7,7-Di trifluoromethyl-3-methoxy-17-methyl-6,8-dioxamorphinan (IXj)

A solution of XXV base (0.01 m) in methylene chloride (50 ml.) is treated with a solution of hexafluoroacetone (0.01 m.) in methylene chloride (25 ml.). After stirring for one hour solid potassium carbonate (0.01 m) is added in portions and stirring continued for about 3 hours. The reaction mixture is washed with water, dried ($K_2CO_3$) and concentrated to give IXj.

EXAMPLE 67

7,7-Ditrifluoromethyl-3-hydroxy-17-methyl-6,8-dioxamorphinan (XVj)

Substitution in the procedure of example 9 for the compound IXa used therein of an equimolar quantity of IXj produces the title compound XVj.

EXAMPLE 68

3-Methoxy-17-methyl-7-(spirocyclohexane)-6,8-dioxamorphinan difumarate (IXk)

A solution of VIIIa base (0.0022 m), cyclohexanone (236 mg.) and p-toluenesulfonic acid (456 mg.) in 50 ml. chloroform was heated at reflux through a Soxhlet extractor containing 4A molecular sieves for 40 hours. This mixture was cooled and treated with dilute potassium carbonate. The chloroform layer was separated, dried ($MgSO_4$), filtered and concentrated to give IXk as an oil. This oil was treated with 2 equivalents of fumaric in 1-propanol to give a crystalline difumarate salt; mp. 202 –204° C.

Anal. Calcd. for $C_{21}H_{29}NO_3 \cdot (C_4H_4O_4)_2$: C, 60.48; H, 6.48; N, 2.44. Found: C, 60.56; H, 6.60; N, 2.40.

EXAMPLE 69

3-Hydroxy-17-methyl-7-(spirocyclohexane)-6,8-dioxamorphinan hydrogen fumarate (Xk)

Compound IXk (base) was 0-demethylated with sodium thioethoxide in dimethyl formamide using the procedure described in example 9. Compound Xk was purified as a crystalline hydrogen fumarate (contains ½ mole of ethyl acetate) from 1-propanol-ethyl acetate; mp. 137°–143° C.

Anal. Calcd. for $C_{20}H_{27}NO_3 \cdot C_4H_4O_4 \cdot (C_4H_8O_2)_{1/2}$: C, 63.79; H, 7.21; N, 2.86. Found: C, 63.79; N, 7.19; N, 3.11.

EXAMPLE 70

17-Cyclopropylmethyl-3-methoxy-7-(spirocyclohexane)-6,8-dioxamorphinan hydrogen fumarate (XIVm)

Compound XIVm was prepared from VIIIf using a procedure similar to that described in example 68. Compound VIXm was isolated as a crystalline hydrogen fumarate from 1-propanol; m.p. 179°–180° C.

Anal. Calcd. for $C_{24}H_{33}NO_3 \cdot C_4H_4O_4$: C, 67.31; H, 7.47; N, 2.80. Found: C, 67.37; H, 7.44; N, 2.77.

EXAMPLE 71

17-Cyclopropylmethyl-3-hydroxy-7-(spirocyclohexane)-6,8-dioxamorphinan fumarate (XVm)

Compound XIVm (base) was 0-demethylated with sodium thioethoxide in dimethyl formamide using the procedure described in example 9. Compound XVm was purified as a crystalline fumarate salt (hydrate) from 1-propanol; m.p. 152°–154° C.

Anal. Calcd. for $(C_{23}H_{31}NO_3)_2 \cdot C_4H_4O_4 \cdot (H_2O)_2$: C, 67.39; H, 7.92; N, 3.14; $H_2O$, 4.05. Found: C, 66.99; H, 7.56; N, 3.14, $H_2O$, 3.53.

We claim:

1. A compound having the formula

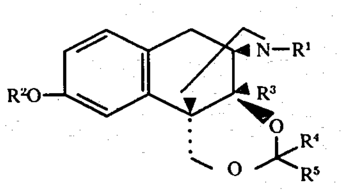

L wherein $R^1$ is selected from the group comprising H,

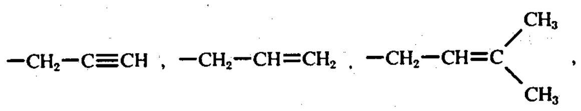

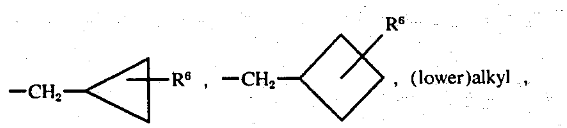

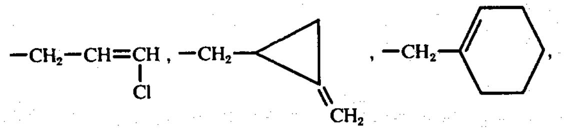

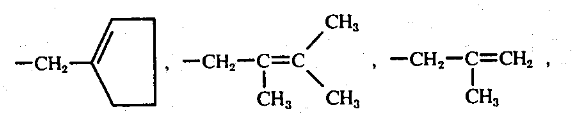

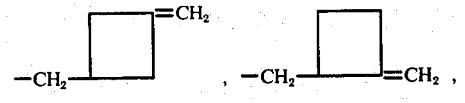

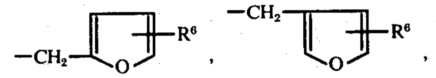

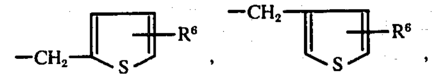

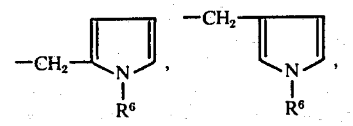

and (lower)alkenyl in which $R^6$ is H or $CH_3$, $R^2$ is selected from the group comprising H, (lower)alkyl,

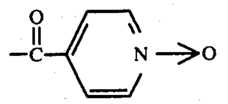

, (lower)alkanoyl ,

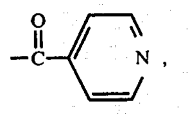

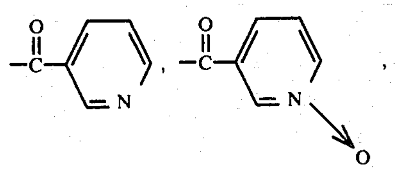

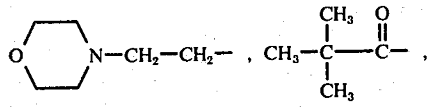

-continued $-CH_2-O-CH_3$ ,

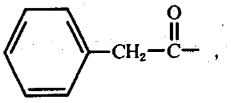

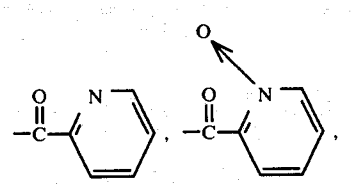

and cinnamoyl, $R^3$ is H or (lower)alkyl and $R^4$ and $R^5$ are alike or different and each is H, (lower)alkyl or trifluoromethyl, or when $R^4$ and $R^5$ are taken together they are a carbonyl or a spirocycloalkyl of 3 to 7 carbon atoms; or a pharmaceutically acceptable acid addition salt thereof.

2. A compound having the formula

XL

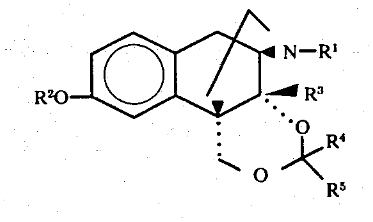

wherein $R^1$ is selected from the group comprising H,

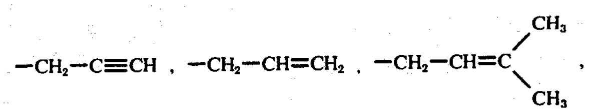

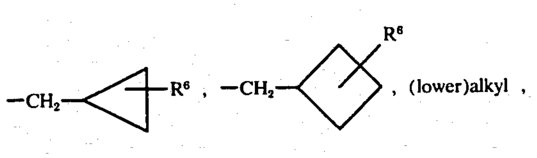

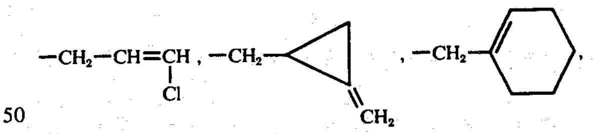

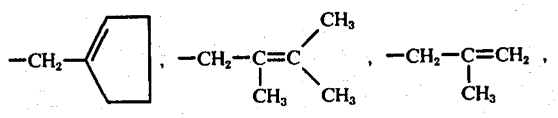

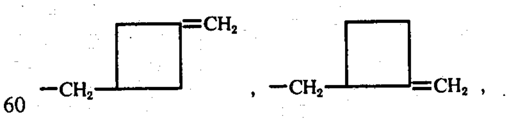

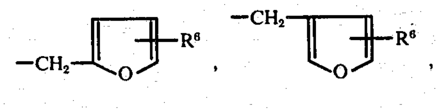

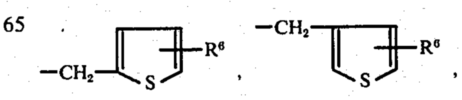

-continued

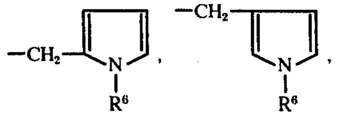

and (lower)alkenyl in which $R^6$ is H or $CH_3$, $R^2$ is selected from the group comprising H, (lower)alkyl,

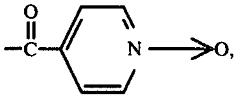
(lower)alkanoyl,
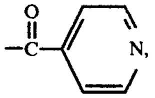

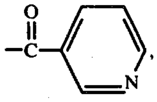
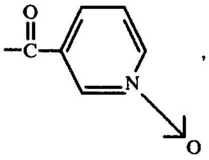
,
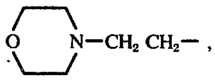

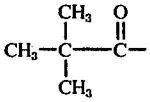
$-CH_2-O-CH_3$,
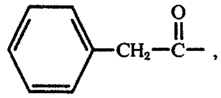

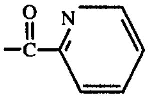
and
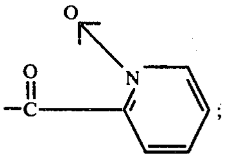
;

and cinnamoyl, $R^3$ is H or (lower)alkyl and $R^4$ and $R^5$ are alike or different and each is H, (lower)alkyl or trifluoromethyl, or when $R^4$ and $R^5$ are taken together they are a carbonyl or a spirocycloalkyl of 3 to 7 carbon atoms; or a pharmaceutically acceptable acid addition salt thereof.

3. A compound of claim 2 wherein $R^1$ is selected from the group comprising H, (lower)alkyl, $-CH_2-C\equiv CH$, $-CH_2-CH=CH_2$,
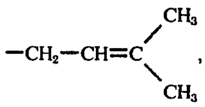
,

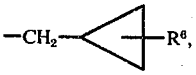
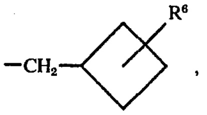
,

-continued

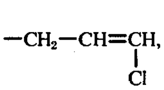
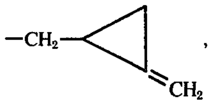
,
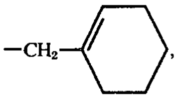

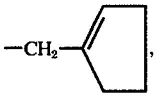
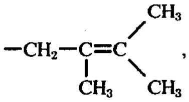
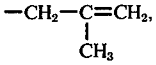

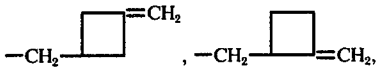

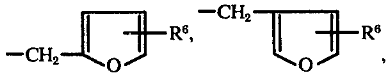

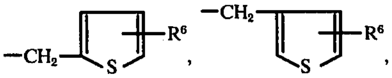

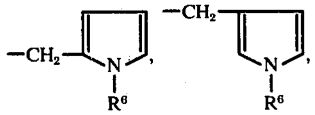

and (lower)alkenyl in which $R^6$ is H or $CH_3$, $R^2$ is selected from the group comprising H, (lower)alkyl,

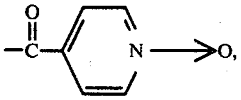
(lower)alkanoyl,
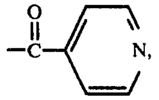

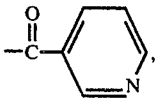
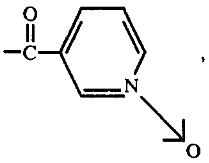
,
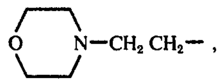

-continued

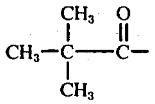 , —$CH_2$—O—$CH_3$, 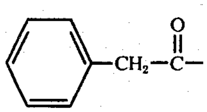 ,

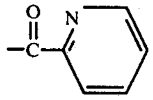 and 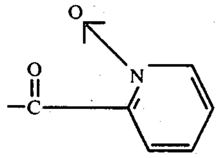 ;

$R^3$ is H, methyl or ethyl and $R^4$ and $R^5$ are alike or different and each is H, methyl, ethyl, trifluoromethyl or when taken together $R^4$ and $R^5$ are a carbonyl or a spirocycloalkyl of 3 to 7 carbon atoms; or a pharmaceutically acceptable acid addition salt thereof.

4. A compound of claim 2 wherein R' is H, -$CH_3$, -$CH_2$-CH=$CH_2$,

—$CH_2$—C≡CH , 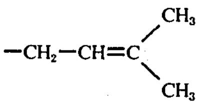 ,

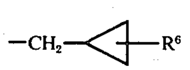 or 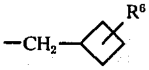

in which $R^6$ is H or $CH_3$, $R^2$ is H, $CH_3$, $CH_3$, 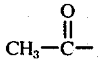 or 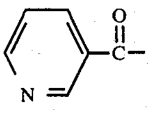 , $R^3$ is H or $CH_3$, $R^4$ and $R^5$ are alike or different and each is H, $CH_3$ or $CF_3$; or a pharmaceutically acceptable acid addition salt thereof.

5. A compound of claim 2 wherein $R^1$ is

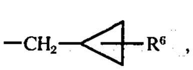 , 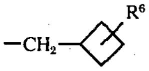

or H, $R^2$ is H or $CH_3$, $R^3$ is H, or $CH_3$, $R^6$ is H or methyl, $R^4$ and $R^5$ are H, $CH_3$ or $CF_3$; or a pharmaceutically acceptable acid addition salt thereof.

6. A compound of claim 5 wherein $R^1$ is cyclopropylmethyl, $R^2$ is H or $CH_3$, $R^3$ is H or $CH_3$, and $R^4$ and $R^5$ are H or $CH_3$; or the hydrochloride, tartrate or fumarate salt thereof.

7. A compound of claim 5 wherein $R^1$ is cyclobutylmethyl, $R^2$ is H or $CH_3$, $R^3$ is H or $CH_3$ and $R^4$ and $R^5$ are H or $CH_3$; or the hydrochloride, tartrate or fumarate salt thereof.

8. A compound of claim 4 wherein $R^1$ is cyclobutylmethyl or cyclopropylmethyl, $R^2$ is H or $CH_3$, $R^3$ is H or $CH_3$, and $R^4$ and $R^5$ taken together are a spirocycloalkyl group of 3 to 7 carbon atoms; or the hydrochloride, tartrate or fumarate salt thereof.

9. A compound of claim 5 wherein $R^1$ is cyclobutylmethyl or cyclopropylmethyl, $R^2$ is H or $CH_3$, $R^3$ is H or $CH_3$, and $R^4$ and $R^5$ are $CF_3$; or the hydrochloride, tartrate or fumarate salt thereof.

10. (±)-17-Cyclopropylmethyl-7,7-dimethyl-3-hydroxy-6,8-dioxamorphinan; or the tartrate, fumarate or hydrochloride salt thereof.

11. (−)-17-Cyclopropylmethyl-7,7-dimethyl-3-hydroxy-6,8-dioxamorphinan; or the tartrate, fumarateor hydrochloride salt thereof.

12. (±)-Clclopropylmethyl-7,7-dimethyl-3-methoxy-6,8-dioxamorphinan; or the tartrate, fumarate or hydrochloride salt thereof.

13. (−)-Cyclopropylmethyl-7,7-dimethyl-3-methoxy-6,8-dioxamorphinan; or the tartrate, fumarate or hydrochloride salt thereof.

14. A compound of claim 5 wherein $R^1$ is cyclopropylmethyl, $R^2$ is H or methyl, $R^3$ is H, $R^4$ and $R^5$ are hydrogen; or the hydrochloride, tartrate or fumarate salt thereof.

15. A compound of claim 2 wherein $R^1$ is H, $R^2$ is H or (lower)alkyl, $R^3$ is H, or $CH_3$ $R^4$ and $R^5$ are alike or different and each is H, (lower)alkyl or $CF_3$, or when taken together $R^4$ and $R^5$ are carbonyl or a spirocycloalkyl of 3 to 7 carbon atoms; or an acid addition salt thereof.

16. A compound of claim 5 wherein $R^1$ is cyclopropylmethyl, $R^2$ is H or $CH_3$, $R^3$ is $CH_3$, $R^4$ and $R^5$ are hydrogen; or the hydrochloride, tartrate or fumarate salt thereof.

17. The essentially pure levorotatory or dextrorotatory isomer of a compound of claim 1.

18. The essentially pure levorotatory or dextrorotatory isomer of a compound of claim 2.

19. The essentially pure levorotatory or dextrorotatory isomer of a compound of claim 3.

20. The essentially pure levorotatory or dextrorotatory isomer of a compound of claim 4.

21. The essentially pure levorotatory or dextrorotatory isomer of a compound of claim 5.

22. The essentially pure levorotatory or dextrorotatory isomer of a compound of claim 14.

23. The essentially pure levorotatory or dextrorotatory isomer of a compound of claim 16.

24. The essentially pure levorotatory isomer of the compound of claim 14 wherein $R^1$ is cyclopropylmethyl, $R^2$, $R^3$, $R^4$ and $R^5$ are H; or the hydrochloride, tartrate or fumarate salt thereof.

25. The essentially pure levorotatory isomer of the compound of claim 16 wherein $R^1$ is cyclopropylmethyl, $R^2$, $R^4$ and $R^5$ are H, and $R^3$ is $CH_3$; or the hydrochloride, tartrate or fumarate salt thereof.

26. The compound having the formula

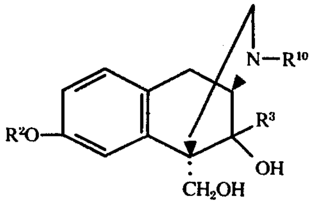

in which $R^{10}$ is

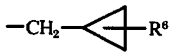 , 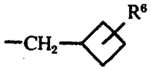

(lower)-alkyl, (lower)alkanoyl,

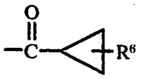 or 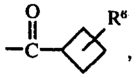 , $R^2$ and $R^3$ are H or (lower)alkyl, and $R^6$ is H or $CH_3$; or an acid addition salt thereof.

27. The compound having the formula

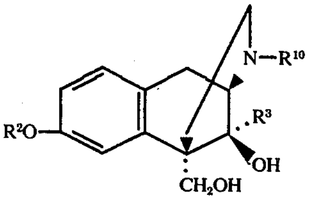

in which $R^{10}$ is

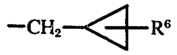 , 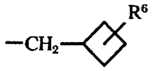

(lower)-alkyl, (lower)alkanoyl,

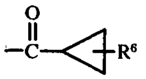 or 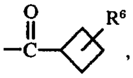 , $R^2$ and $R^3$ are H or (lower)alkyl, and $R^6$ is H or methyl; or an acid addition salt thereof.

28. The compound of the formula

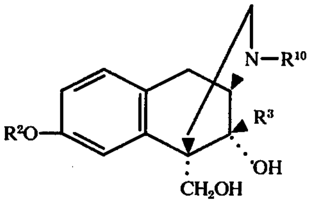

in which $R^{10}$ is

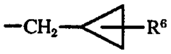 , 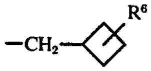

(lower)alkyl, (lower)alkanoyl,

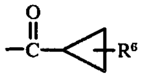 or 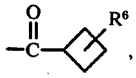 , $R^2$ and $R^3$ are H or (lower)alkyl, and $R^6$ is H or $CH_3$; or an acid addition salt thereof.

* * * * *

UNITED STATES PATENT AND TRADEMARK OFFICE

CERTIFICATE OF CORRECTION

PATENT NO. : 4,016,167

DATED : April 5, 1977

INVENTOR(S) : Thomas A. Montzka and John D. Matiskella

It is certified that error appears in the above-identified patent and that said Letters Patent are hereby corrected as shown below:

In Claim 1, the first structural formula should read

-- 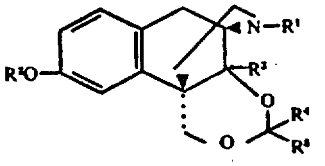 --.

In Claim 4, line 6 thereof, delete "$CH_3$,".

In Claim 11, bridging lines 2 and 3 thereof, "fumarateor" should read --fumarate or--.

In Claim 12, line 1 thereof, "Clclopropylmethyl" should read --Cyclopropylmethyl--.

Signed and Sealed this

*nineteenth* Day of *July 1977*

[SEAL]

*Attest:*

RUTH C. MASON
*Attesting Officer*

C. MARSHALL DANN
*Commissioner of Patents and Trademarks*